US012770250B2

(12) United States Patent
Fujii et al.

(10) Patent No.: US 12,770,250 B2
(45) Date of Patent: Oct. 20, 2026

(54) INFORMATION PROCESSING SYSTEM, INFORMATION PROCESSING METHOD, AND PROGRAM

(71) Applicants: GENOMEDIA INC., Tokyo (JP); NATIONAL CANCER CENTER, Tokyo (JP)

(72) Inventors: Satoshi Fujii, Chiba (JP); Takayuki Yoshino, Chiba (JP); Tomoyuki Yamada, Tokyo (JP); Masahiro Hattori, Tokyo (JP)

(73) Assignees: GENOMEDIA INC., Tokyo (JP); NATIONAL CANCER CENTER, Tokyo (JP)

( * ) Notice: Subject to any disclaimer, the term of this patent is extended or adjusted under 35 U.S.C. 154(b) by 603 days.

(21) Appl. No.: 18/248,706

(22) PCT Filed: Oct. 14, 2020

(86) PCT No.: PCT/JP2020/038843
§ 371 (c)(1),
(2) Date: Apr. 12, 2023

(87) PCT Pub. No.: WO2022/079847
PCT Pub. Date: Apr. 21, 2022

(65) Prior Publication Data

US 2023/0274428 A1 Aug. 31, 2023

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06V 10/267* (2022.01); (Continued)

(58) Field of Classification Search
None
See application file for complete search history.

(56) References Cited

U.S. PATENT DOCUMENTS

2018/0204324 A1 7/2018 Kawaguchi et al.
2018/0232883 A1 8/2018 Sethi et al.
(Continued)

FOREIGN PATENT DOCUMENTS

CN 106355023 A 1/2017
CN 110660055 A 1/2020
(Continued)

OTHER PUBLICATIONS

Chinese Office Action issued in Chinese Patent Application No. 202080106293.5 dated May 24, 2025.
(Continued)

*Primary Examiner* — David Ometz
(74) *Attorney, Agent, or Firm* — McDonald Hopkins LLC

(57) ABSTRACT

An information processing system including units configured to: acquire a pathologic tissue image of a patient having a target disease; divide the pathologic tissue image into region images; input each of the region images to each of a plurality of feature prediction models constructed one-to-one for types of histopathological features; sort a plurality of region images of which respective combinations of presence or absence of the histopathological features based on the acquisition match a previously set combination of presence or absence of the histopathological features at time of sorting; input each of the region images selected by the sorting to each of gene mutation prediction models constructed one-to-one for types of gene mutations, the gene mutation prediction models each having a combination of presence or absence of the histopathological features; and
(Continued)

output a prediction result of presence or absence of at least one gene mutation in the patient.

16 Claims, 23 Drawing Sheets

(51) Int. Cl.

| | |
|---|---|
| ***G06V 10/26*** | (2022.01) |
| ***G06V 10/77*** | (2022.01) |
| ***G06V 20/69*** | (2022.01) |
| ***G16B 20/20*** | (2019.01) |
| ***G16B 40/20*** | (2019.01) |

(52) U.S. Cl.

CPC ........ *G06V 10/7715* (2022.01); *G06V 20/695* (2022.01); *G16B 20/20* (2019.02); *G16B 40/20* (2019.02); *G06T 2207/30028* (2013.01); *G06T 2207/30096* (2013.01); *G06V 2201/031* (2022.01)

(56) References Cited

U.S. PATENT DOCUMENTS

| | | | | |
|---|---|---|---|---|
| 2020/0105413 | A1* | 4/2020 | Vladimirova | G16H 20/30 |
| 2020/0184643 | A1* | 6/2020 | Coudray | G06V 20/698 |
| 2021/0035300 | A1 | 2/2021 | Wakai et al. | |

FOREIGN PATENT DOCUMENTS

| | | | | | |
|---|---|---|---|---|---|
| CN | 111369534 | A | | 7/2020 | |
| CN | 111370128 | A | * | 7/2020 | G06N 3/045 |
| JP | 2011215680 | A | | 10/2011 | |
| WO | 2017/010397 | A1 | | 1/2017 | |
| WO | 2016104794 | A1 | | 10/2017 | |
| WO | WO-2018207261 | A1 | * | 11/2018 | G06T 7/66 |
| WO | 2019/159821 | A1 | | 8/2019 | |

OTHER PUBLICATIONS

Chinese Office Action issued in Chinese Patent Application No. 202080106293.5 dated Oct. 30, 2024.

European Search Report for Application No. 20957676.8 issued on Jul. 4, 2024.

Daisuke Komura et al: "Machine Learning Methods for Histopathological Image Analysis", Computational and Structural Biotechnology Journal, vol. 16, Jan. 1, 2018, pp. 34-42, Sweden.

Andrew J. Schaumberg et al: "H&E-stained Whole Slide Image Deep Learning Predicts SPOP Mutation State in Prostate Cancer", bioRXiv, Oct. 1, 2018.

Muller Mike Fetal: "Molecular pathological classification of colorectal cancer", Virchows Archiv, Springer Berlin Heidelberg, Berlin/Heidelberg, vol. 469, No. 2, Jun. 20, 2016 (Jun. 20, 2016), pp. 125-134.

Yan Xu et al: "Large scale tissue histopathology image classification, segmentation, and visualization via deep convolutional activation features", BMC Bioinformatics, Biomed Central Ltd, London, UK, vol. 18 No. 1, May 26, 2017, pp. 1-17.

Japanese Office Action for Application No. 2022-556767 Issued on Sep. 3, 2024.

International Search Report dated Jan. 12, 2021 issued in PCT/JP2020/038843.

Written Opinion dated Jan. 12, 2021 issued in PCT/JP2020/038843.

Nicolas Coudray, et al., "Classification and mutation prediction from non-small cell lung cancer histopathology images using deep learning", Nature Medicine, vol. 24, pp. 1559-1567, (2018). https://doi.org/10.1038/s41591-018-0177-5.

https://ganjoho.jp/public/dia_tre/treatment/genomic_medicine/gentest02.html.

Fu, Yu, Jung, A.W., Torne, R.V. et al., "Pan-cancer computational histopathology reveals mutations, tumor composition and prognosis", Nature Cancer, vol. 1, pp. 800-810, Aug. 2020, https://doi.org/10.1038/s43018-020-0085-8.

Office Action dated Mar. 31, 2026. Japanese Patent Application No. 2025-065843. 4 pages.

* cited by examiner

LEARNING PROCESS

FIG.9

| | | SECOND-TERM TEST DATA | | FIRST-TERM DATA | | 2.5-TERM DATA | | TCGA DATA | |
|---|---|---|---|---|---|---|---|---|---|
| | | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) |
| PRIMARY LESION SITE | COMBINATION OF PRESENCE OR ABSENCE OF HISTOPATHOLOGICAL FEATURES AT TIME OF SORTING | AUC | AUC | AUC | AUC | AUC | AUC | AUC | AUC |
| LARGE INTESTINE LEFT PART | TUMOR-CELL RATIO LARGER THAN 80% | 0.83245 | 0.83777 | | | | | 0.89834 | 0.89267 |
| LARGE INTESTINE LEFT PART | PAPILLARY STRUCTURE | 0.85106 | 0.85727 | | | | | 0.90157 | 0.88976 |
| LARGE INTESTINE LEFT PART | NON-SERRATED AND PAPILLARY STRUCTURE | 0.85106 | 0.85727 | | | | | 0.90157 | 0.88976 |
| LARGE INTESTINE LEFT PART | NON-SERRATED AND PAPILLARY STRUCTURE AND MUCUS PRESENT | | 0.80645 | | | | | 0.94417 | 0.97816 |
| LARGE INTESTINE LEFT PART | CRIBRIFORM STRUCTURE | | 0.80309 | | | | | 0.93714 | 0.94521 |
| LARGE INTESTINE LEFT PART | CRIBRIFORM STRUCTURE AND NO MUCUS PRESENT | 0.89873 | 0.88397 | | | | | 0.84414 | 0.82345 |
| LARGE INTESTINE LEFT PART | CRIBRIFORM STRUCTURE AND MUCUS PRESENT | 0.83951 | 0.83539 | | | | | 0.80686 | 0.80196 |

FIG.10

| | | SECOND-TERM TEST DATA | | FIRST-TERM DATA | | 2.5-TERM DATA | | TCGA DATA | |
|---|---|---|---|---|---|---|---|---|---|
| | | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) |
| PRIMARY LESION SITE | COMBINATION OF PRESENCE OR ABSENCE OF HISTOPATHOLOGICAL FEATURES AT TIME OF SORTING | AUC | AUC | AUC | AUC | AUC | AUC | AUC | AUC |
| LARGE INTESTINE LEFT PART | RAIL PATTERN | | 0.81275 | | | | | 0.87811 | 0.86994 |
| LARGE INTESTINE LEFT PART | SMALL SOLID NEST | 0.87500 | 0.84167 | | | | | 1.00000 | 1.00000 |
| LARGE INTESTINE LEFT PART | SMALL SOLID NEST AND TYPICAL CELLS | 0.80435 | | | | | | | 1.00000 |
| LARGE INTESTINE LEFT PART | LARGE SOLID NEST AND TYPICAL CELLS | | 0.81466 | | | | | 0.97093 | 0.98256 |
| LARGE INTESTINE LEFT PART | ELONGATED ELLIPTIC NUCLEUS | 0.82480 | 0.82283 | | | | | 0.86357 | 0.87950 |
| LARGE INTESTINE LEFT PART | MUCUS PRESENT | 0.88333 | 0.88333 | 0.84884 | 0.86047 | | | | |
| LARGE INTESTINE LEFT PART | NON-SERRATED AND PAPILLARY STRUCTURE AND NO MUCUS PRESENT | 0.85882 | 0.84706 | 0.80612 | 0.80612 | | | | |
| LARGE INTESTINE LEFT PART | CRIBRIFORM STRUCTURE AND NO MUCUS PRESEN | 0.82432 | 0.81982 | 0.84589 | 0.84589 | | | | |
| LARGE INTESTINE LEFT PART | CRIBRIFORM STRUCTURE AND MUCUS PRESENT | | 0.80317 | | | | | 0.83293 | 0.82403 |

FIG.11

| | | SECOND-TERM TEST DATA | | FIRST-TERM DATA | | 2.5-TERM DATA | | TCGA DATA | |
|---|---|---|---|---|---|---|---|---|---|
| | | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) |
| PRIMARY LESION SITE | COMBINATION OF PRESENCE OR ABSENCE OF HISTOPATHOLOGICAL FEATURES AT TIME OF SORTING | AUC | AUC | AUC | AUC | AUC | AUC | AUC | AUC |
| LARGE INTESTINE RIGHT PART | TRABECULAR STRUCTURE AND MUCUS PRESENT | | 0.80405 | | | 0.86486 | 0.83108 | | |
| LARGE INTESTINE RIGHT PART | TRABECULAR STRUCTURE AND MUCUS LEAKAGE | 0.88333 | | | | 0.89796 | 0.96939 | | |

FIG.12

| | | SECOND-TERM TEST DATA | | FIRST-TERM DATA | | 2.5-TERM DATA | | TCGA DATA | |
|---|---|---|---|---|---|---|---|---|---|
| | | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) |
| PRIMARY LESION SITE | COMBINATION OF PRESENCE OR ABSENCE OF HISTOPATHOLOGICAL FEATURES AT TIME OF SORTING | AUC | AUC | AUC | AUC | AUC | AUC | AUC | AUC |
| LARGE INTESTINE RIGHT PART | SIGNET RING CELL AND MUCUS LEAKAGE | 0.95238 | 0.90476 | 0.84615 | 0.83654 | | | | |
| LARGE INTESTINE RIGHT PART | GERM CELL | 1.00000 | | | | | | 1.00000 | 1.00000 |
| LARGE INTESTINE LEFT PART | TRABECULAR STRUCTURE AND NO MUCUS PRESENT | 0.88889 | 0.88889 | | | 1.00000 | | | |
| LARGE INTESTINE LEFT PART | MUCUS LEAKAGE | 0.90909 | 0.90909 | | | | | 0.84211 | 0.83083 |
| LARGE INTESTINE LEFT PART | GERM CELL | 0.83333 | 0.83333 | 0.87500 | | | | | |

FIG.13

| | | SECOND-TERM TEST DATA | | FIRST-TERM DATA | | 2.5-TERM DATA | | TCGA DATA | |
|---|---|---|---|---|---|---|---|---|---|
| | | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) |
| PRIMARY LESION SITE | COMBINATION OF PRESENCE OR ABSENCE OF HISTOPATHOLOGICAL FEATURES AT TIME OF SORTING | AUC | AUC | AUC | AUC | AUC | AUC | AUC | AUC |
| LARGE INTESTINE LEFT PART | RAIL PATTERN | 0.90323 | 0.82796 | | | | | 0.83636 | |
| LARGE INTESTINE LEFT PART | TRABECULAR STRUCTURE AND NO MUCUS PRESENT | 0.82353 | 0.88235 | | | 0.81481 | 0.84444 | | |
| LARGE INTESTINE LEFT PART | TUMOR-CELL RATIO LARGER THAN 50% | 0.94382 | 0.92135 | | | | | | 0.80667 |
| LARGE INTESTINE LEFT PART | SOLID NEST | | 0.80851 | | | | | 1.00000 | 1.00000 |
| LARGE INTESTINE LEFT PART | SMALL SOLID NEST AND TYPICAL CELLS | 0.94253 | 0.94253 | | | | | 0.95455 | 0.95455 |
| LARGE INTESTINE LEFT PART | ELONGATED ELLIPTIC NUCLEUS | 0.87107 | 0.86792 | | | 0.90392 | 0.90196 | | |
| LARGE INTESTINE LEFT PART | PAPILLARY STRUCTURE | 0.82593 | 0.82778 | 0.81500 | 0.83000 | | | | |
| LARGE INTESTINE LEFT PART | GERM CELL | 0.93103 | 0.87931 | | | 0.87805 | 0.87805 | 0.80952 | |
| LARGE INTESTINE LEFT PART | NON-SERRATED AND PAPILLARY STRUCTURE | 0.82593 | 0.82778 | 0.81500 | 0.83000 | | | | |
| LARGE INTESTINE LEFT PART | ROUNDISH NUCLEUS | 0.84277 | 0.83333 | | | 0.87751 | 0.84137 | | |
| LARGE INTESTINE LEFT PART | CRIBRIFORM STRUCTURE AND NO MUCUS PRESENT | 0.98780 | 0.98780 | | | | | 0.96154 | 0.93846 |
| LARGE INTESTINE LEFT PART | CRIBRIFORM STRUCTURE AND MUCUS PRESENT | 0.96250 | 0.95000 | | | | | 0.93333 | 0.91111 |
| LARGE INTESTINE LEFT PART | CRIBRIFORM STRUCTURE AND MUCUS LEAKAGE | 0.84746 | 0.83729 | 0.91548 | 0.90408 | | | | |

FIG.14

| PRIMARY LESION SITE | COMBINATION OF PRESENCE OR ABSENCE OF HISTOPATHOLOGICAL FEATURES AT TIME OF SORTING | SECOND-TERM TEST DATA | | FIRST-TERM DATA | | 2.5-TERM DATA | | TCGA DATA | |
|---|---|---|---|---|---|---|---|---|---|
| | | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) |
| | | AUC | AUC | AUC | AUC | AUC | AUC | AUC | AUC |
| LARGE INTESTINE LEFT PART | SIGNET RING CELL AND MUCUS LEAKAGE | | 0.87500 | | | | 0.80000 | | |
| LARGE INTESTINE LEFT PART | TUBULAR STRUCTURE AND NO MUCUS PRESENT | 0.91772 | 0.91772 | 0.80609 | | | | | |
| LARGE INTESTINE LEFT PART | TRABECULAR STRUCTURE AND NO MUCUS PRESENT | 0.97619 | 0.89286 | | | | 0.80741 | | |
| LARGE INTESTINE LEFT PART | SMALL SOLID NEST | 0.80000 | | | | 0.85973 | 0.83710 | | |
| LARGE INTESTINE LEFT PART | LARGE SOLID NEST | | 0.83871 | | 0.80952 | | | | |
| LARGE INTESTINE LEFT PART | LARGE SOLID NEST AND TYPICAL CELLS | 0.80250 | | | | | | 0.91111 | 0.88444 |
| LARGE INTESTINE LEFT PART | PAPILLARY STRUCTURE | 0.82331 | | | | | | 0.87895 | 0.86316 |
| LARGE INTESTINE LEFT PART | NO MUCUS PRESENT | 1.00000 | 1.00000 | | | 0.91667 | 0.86806 | | |
| LARGE INTESTINE LEFT PART | MUCUS PRESENT | 0.80000 | | 0.86667 | 0.86667 | | | | |
| LARGE INTESTINE LEFT PART | GERM CELL | 0.88835 | 0.86893 | | | | | 0.99585 | 0.91494 |
| LARGE INTESTINE LEFT PART | NON-SERRATED AND PAPILLARY STRUCTURE | 0.82331 | | | | | | 0.87895 | 0.86316 |
| LARGE INTESTINE LEFT PART | NON-SERRATED AND PAPILLARY STRUCTURE AND NO MUCUS PRESENT | 0.88144 | 0.90206 | | | 0.81669 | 0.81847 | | |
| LARGE INTESTINE LEFT PART | NON-SERRATED AND PAPILLARY STRUCTURE AND MUCUS PRESENT | 0.80233 | | | | 0.92537 | 0.94030 | | |
| LARGE INTESTINE LEFT PART | CRIBRIFORM STRUCTURE | 0.86947 | 0.86283 | | | | | 0.81046 | |
| LARGE INTESTINE LEFT PART | CRIBRIFORM STRUCTURE AND NO MUCUS PRESENT | 0.80000 | | | | | | 0.88235 | 0.85294 |
| LARGE INTESTINE LEFT PART | CRIBRIFORM STRUCTURE AND MUCUS PRESENT | 0.87356 | 0.84866 | | | | | 0.92593 | 0.94444 |
| LARGE INTESTINE LEFT PART | CRIBRIFORM STRUCTURE AND MUCUS LEAKAGE | 0.82051 | 0.84615 | | | 0.92500 | 0.95000 | | |
| LARGE INTESTINE LEFT PART | BUDDING PRESENT | 0.82275 | | 0.87865 | 0.87263 | 0.80117 | | | |
| LARGE INTESTINE LEFT PART | TUMOR-CELL RATIO LARGER THAN 50% | 0.92553 | 0.90426 | | | | | 0.86093 | 0.83996 |
| LARGE INTESTINE LEFT PART | SMALL SOLID NEST | 0.80303 | 0.81818 | 0.91257 | 0.92896 | 0.87500 | 0.87500 | | |
| LARGE INTESTINE LEFT PART | SMALL SOLID NEST AND TYPICAL CELLS | 0.81875 | 0.83750 | | | | | | 0.80556 |
| LARGE INTESTINE LEFT PART | LARGE SOLID NEST | 1.00000 | 1.00000 | | | | | 0.94697 | 0.93939 |
| LARGE INTESTINE LEFT PART | LARGE SOLID NEST AND TYPICAL CELLS | 0.81818 | 0.82386 | | | | | 0.88889 | 0.86111 |
| LARGE INTESTINE LEFT PART | ELONGATED ELLIPTIC NUCLEUS | 0.92929 | 0.92929 | | | | | | 0.81901 |
| LARGE INTESTINE LEFT PART | MUCUS PRESENT | 0.90000 | 0.95000 | | | | | 1.00000 | 1.00000 |
| LARGE INTESTINE LEFT PART | MUCUS LEAKAGE | 0.86765 | 0.86765 | | | | | 1.00000 | 0.95833 |
| LARGE INTESTINE LEFT PART | NON-SERRATED AND PAPILLARY STRUCTURE AND NO MUCUS PRESENT | | 0.80983 | 0.85753 | 0.83871 | | | | |
| LARGE INTESTINE LEFT PART | CRIBRIFORM STRUCTURE | 0.95522 | 0.94030 | | | | | 0.82184 | |
| LARGE INTESTINE LEFT PART | CRIBRIFORM STRUCTURE AND NO MUCUS PRESENT | 0.81500 | 0.80500 | 0.84120 | 0.83262 | 0.92239 | 0.91940 | | |
| LARGE INTESTINE LEFT PART | CRIBRIFORM STRUCTURE AND MUCUS PRESENT | 0.98765 | 0.98765 | | | | | 0.83429 | 0.84163 |

FIG.15

| | | SECOND-TERM TEST DATA | | FIRST-TERM DATA | | 2.5-TERM DATA | | TCGA DATA | |
|---|---|---|---|---|---|---|---|---|---|
| | | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) | CASE IMPORT METHOD (1) | CASE IMPORT METHOD (2) |
| PRIMARY LESION SITE | COMBINATION OF PRESENCE OR ABSENCE OF HISTOPATHOLOGICAL FEATURES AT TIME OF SORTING | AUC | AUC | AUC | AUC | AUC | AUC | AUC | AUC |
| LARGE INTESTINE LEFT PART | TUBULAR STRUCTURE AND MUCUS PRESENT | 0.89925 | 0.93843 | | | 0.83990 | 0.84843 | | |
| LARGE INTESTINE LEFT PART | TUBULAR STRUCTURE AND MUCUS LEAKAGE | 0.88235 | 0.87353 | | | 0.83125 | 0.84141 | | |
| LARGE INTESTINE LEFT PART | RAIL PATTERN | 0.89706 | 0.91912 | | | 0.80357 | | | |
| LARGE INTESTINE LEFT PART | HIGH-GRADE CELL ATYPIA | 0.83962 | 0.83019 | 0.83592 | | 0.82371 | 0.83587 | | |
| LARGE INTESTINE LEFT PART | TRABECULAR STRUCTURE AND MUCUS PRESENT | | 0.80405 | | | 0.86486 | 0.83108 | | |
| LARGE INTESTINE LEFT PART | TRABECULAR STRUCTURE AND MUCUS LEAKAGE | 0.88333 | | | | 0.89796 | 0.96939 | | |
| LARGE INTESTINE LEFT PART | TUMOR-CELL RATIO LARGER THAN 50% | 0.87292 | 0.88229 | | | 0.83965 | 0.84428 | 0.86533 | 0.90578 |
| LARGE INTESTINE LEFT PART | SOLID NEST | 0.96875 | 0.96094 | | | 0.94253 | 0.95402 | | |
| LARGE INTESTINE LEFT PART | SMALL SOLID NEST | 0.86667 | | | | 0.94444 | 0.89583 | | |
| LARGE INTESTINE LEFT PART | SMALL SOLID NEST AND TYPICAL CELLS | 0.80000 | | | | 0.95455 | 0.90909 | | |
| LARGE INTESTINE LEFT PART | LARGE SOLID NEST | 0.84091 | 0.84091 | | | 0.85354 | 0.85227 | | |
| LARGE INTESTINE LEFT PART | LARGE SOLID NEST AND TYPICAL CELLS | 0.93333 | 0.86667 | | | 0.83333 | 0.83333 | | |
| LARGE INTESTINE LEFT PART | ELONGATED ELLIPSE | | 0.80204 | | | 0.93478 | 0.94348 | | |
| LARGE INTESTINE LEFT PART | PAPILLARY STRUCTURE | 0.88750 | 0.87411 | | | | | 0.93780 | 0.98565 |
| LARGE INTESTINE LEFT PART | MUCUS PRESENT | 0.96196 | 0.94293 | | | | | 0.90668 | 0.89475 |
| LARGE INTESTINE LEFT PART | MUCUS LEAKAGE | 0.80104 | | 0.86351 | 0.86689 | 0.89268 | 0.88573 | | |
| LARGE INTESTINE LEFT PART | NON-SERRATED AND PAPILLARY STRUCTURE | 0.88750 | 0.87411 | | | | | 0.93780 | 0.98565 |
| LARGE INTESTINE LEFT PART | NON-SERRATED AND PAPILLARY STRUCTURE AND NO MUCUS PRESENT | 0.82710 | 0.83411 | | | | 0.80791 | | |
| LARGE INTESTINE LEFT PART | NON-SERRATED AND PAPILLARY STRUCTURE AND MUCUS PRESENT | 0.85274 | 0.82106 | | | | | 0.88767 | 0.90084 |
| LARGE INTESTINE LEFT PART | ROUNDISH NUCLEUS | 0.98980 | 0.98980 | | | | | 0.88372 | 0.88372 |
| LARGE INTESTINE LEFT PART | CRIBRIFORM STRUCTURE | 0.85294 | 0.85294 | | | 0.81341 | 0.81214 | | |
| LARGE INTESTINE LEFT PART | CRIBRIFORM STRUCTURE AND NO MUCUS PRESENT | 0.88710 | 0.88710 | | | | | 0.81818 | 0.87879 |
| LARGE INTESTINE LEFT PART | CRIBRIFORM STRUCTURE AND MUCUS PRESENT | | 0.80847 | | | | | 0.82600 | 0.80596 |
| LARGE INTESTINE LEFT PART | CRIBRIFORM STRUCTURE AND MUCUS PRESENT | 1.00000 | 1.00000 | | | | | 1.00000 | 0.98507 |
| LARGE INTESTINE LEFT PART | CRIBRIFORM STRUCTURE AND MUCUS LEAKAGE | 0.86462 | 0.84308 | | | 0.82933 | 0.85171 | 0.81844 | 0.83480 |
| LARGE INTESTINE LEFT PART | BUDDING PRESENT | 0.85000 | 1.00000 | | | 0.84444 | 0.86667 | | |

FIG.16

T1: BRAF TABLE

| PRIMARY LESION SITE | COMBINATION OF PRESENCE OR ABSENCE OF HISTOPATHOLOGICAL FEATURES AT TIME OF SORTING |
|---|---|
| LARGE INTESTINE LEFT PART | TUMOR-CELL RATIO LARGER THAN 50% |
| LARGE INTESTINE LEFT PART | PAPILLARY STRUCTURE |
| LARGE INTESTINE LEFT PART | NON-SERRATED AND PAPILLARY STRUCTURE |
| LARGE INTESTINE LEFT PART | NON-SERRATED AND PAPILLARY STRUCTURE AND MUCUS PRESENT |
| LARGE INTESTINE LEFT PART | CRIBRIFORM STRUCTURE |
| LARGE INTESTINE LEFT PART | CRIBRIFORM STRUCTURE AND NO MUCUS PRESENT |
| LARGE INTESTINE LEFT PART | CRIBRIFORM STRUCTURE AND MUCUS PRESENT |

T2: BRAF V600E TABLE

| PRIMARY LESION SITE | COMBINATION OF PRESENCE OR ABSENCE OF HISTOPATHOLOGICAL FEATURES AT TIME OF SORTING |
|---|---|
| LARGE INTESTINE LEFT PART | RAIL PATTERN |
| LARGE INTESTINE LEFT PART | SMALL SOLID NEST |
| LARGE INTESTINE LEFT PART | SMALL SOLID NEST AND TYPICAL CELLS |
| LARGE INTESTINE LEFT PART | LARGE SOLID NEST AND TYPICAL CELLS |
| LARGE INTESTINE LEFT PART | ELONGATED ELLIPTIC NUCLEUS |
| LARGE INTESTINE LEFT PART | MUCUS PRESENT |
| LARGE INTESTINE LEFT PART | NON-SERRATED AND PAPILLARY STRUCTURE AND NO MUCUS PRESENT |
| LARGE INTESTINE LEFT PART | CRIBRIFORM STRUCTURE AND NO MUCUS PRESENT |
| LARGE INTESTINE LEFT PART | CRIBRIFORM STRUCTURE AND MUCUS PRESENT |

T3: ERBB2 TABLE

| PRIMARY LESION SITE | COMBINATION OF PRESENCE OR ABSENCE OF HISTOPATHOLOGICAL FEATURES AT TIME OF SORTING |
|---|---|
| LARGE INTESTINE RIGHT PART | TRABECULAR STRUCTURE AND MUCUS PRESENT |
| LARGE INTESTINE RIGHT PART | TRABECULAR STRUCTURE AND MUCUS LEAKAGE |

T4: TP53 TABLE

| PRIMARY LESION SITE | COMBINATION OF PRESENCE OR ABSENCE OF HISTOPATHOLOGICAL FEATURES AT TIME OF SORTING |
|---|---|
| LARGE INTESTINE RIGHT PART | SIGNET RING CELL AND MUCUS LEAKAGE |
| LARGE INTESTINE RIGHT PART | GERM CELL |
| LARGE INTESTINE LEFT PART | TRABECULAR STRUCTURE AND NO MUCUS PRESENT |
| LARGE INTESTINE LEFT PART | MUCUS LEAKAGE |
| LARGE INTESTINE LEFT PART | GERM CELL |

T5: MSI TABLE

| PRIMARY LESION SITE | COMBINATION OF PRESENCE OR ABSENCE OF HISTOPATHOLOGICAL FEATURES AT TIME OF SORTING |
|---|---|
| LARGE INTESTINE LEFT PART | RAIL PATTERN |
| LARGE INTESTINE LEFT PART | TRABECULAR STRUCTURE AND NO MUCUS PRESENT |
| LARGE INTESTINE LEFT PART | TUMOR-CELL RATIO LARGER THAN 50% |
| LARGE INTESTINE LEFT PART | SOLID NEST |
| LARGE INTESTINE LEFT PART | SMALL SOLID NEST AND TYPICAL CELLS |
| LARGE INTESTINE LEFT PART | ELONGATED ELLIPTIC NUCLEUS |
| LARGE INTESTINE LEFT PART | PAPILLARY STRUCTURE |
| LARGE INTESTINE LEFT PART | GERM CELL |
| LARGE INTESTINE LEFT PART | NON-SERRATED AND PAPILLARY STRUCTURE |
| LARGE INTESTINE LEFT PART | ROUNDISH NUCLEUS |
| LARGE INTESTINE LEFT PART | CRIBRIFORM STRUCTURE AND NO MUCUS PRESENT |
| LARGE INTESTINE LEFT PART | CRIBRIFORM STRUCTURE AND MUCUS PRESENT |
| LARGE INTESTINE LEFT PART | CRIBRIFORM STRUCTURE AND MUCUS LEAKAGE |

FIG.17

T6: RAS TABLE

| PRIMARY LESION SITE | COMBINATION OF PRESENCE OR ABSENCE OF HISTOPATHOLOGICAL FEATURES AT TIME OF SORTING |
|---|---|
| LARGE INTESTINE LEFT PART | SIGNET RING CELL AND MUCUS LEAKAGE |
| LARGE INTESTINE LEFT PART | TUBULAR STRUCTURE AND NO MUCUS PRESENT |
| LARGE INTESTINE LEFT PART | TRABECULAR STRUCTURE AND NO MUCUS PRESENT |
| LARGE INTESTINE LEFT PART | SMALL SOLID NEST |
| LARGE INTESTINE LEFT PART | LARGE SOLID NEST |
| LARGE INTESTINE LEFT PART | LARGE SOLID NEST AND TYPICAL CELLS |
| LARGE INTESTINE LEFT PART | PAPILLARY STRUCTURE |
| LARGE INTESTINE LEFT PART | NO MUCUS PRESENT |
| LARGE INTESTINE LEFT PART | MUCUS PRESENT |
| LARGE INTESTINE LEFT PART | GERM CELL |
| LARGE INTESTINE LEFT PART | NON-SERRATED AND PAPILLARY STRUCTURE |
| LARGE INTESTINE LEFT PART | NON-SERRATED AND PAPILLARY STRUCTURE AND NO MUCUS PRESENT |
| LARGE INTESTINE LEFT PART | NON-SERRATED AND PAPILLARY STRUCTURE AND MUCUS PRESENT |
| LARGE INTESTINE LEFT PART | CRIBRIFORM STRUCTURE |
| LARGE INTESTINE LEFT PART | CRIBRIFORM STRUCTURE AND NO MUCUS PRESENT |
| LARGE INTESTINE LEFT PART | CRIBRIFORM STRUCTURE AND MUCUS PRESENT |
| LARGE INTESTINE LEFT PART | CRIBRIFORM STRUCTURE AND MUCUS LEAKAGE |
| LARGE INTESTINE LEFT PART | BUDDING PRESENT |
| LARGE INTESTINE LEFT PART | TUMOR-CELL RATIO LARGER THAN 50% |
| LARGE INTESTINE LEFT PART | SMALL SOLID NEST |
| LARGE INTESTINE LEFT PART | SMALL SOLID NEST AND TYPICAL CELLS |
| LARGE INTESTINE LEFT PART | LARGE SOLID NEST |
| LARGE INTESTINE LEFT PART | LARGE SOLID NEST AND TYPICAL CELLS |
| LARGE INTESTINE LEFT PART | ELONGATED ELLIPTIC NUCLEUS |
| LARGE INTESTINE LEFT PART | MUCUS PRESENT |
| LARGE INTESTINE LEFT PART | MUCUS LEAKAGE |
| LARGE INTESTINE LEFT PART | NON-SERRATED AND PAPILLARY STRUCTURE AND NO MUCUS PRESENT |
| LARGE INTESTINE LEFT PART | CRIBRIFORM STRUCTURE |
| LARGE INTESTINE LEFT PART | CRIBRIFORM STRUCTURE AND NO MUCUS PRESENT |
| LARGE INTESTINE LEFT PART | CRIBRIFORM STRUCTURE AND MUCUS PRESENT |

INCLUDED IN RAS TABLE T6

| PRIMARY LESION SITE | COMBINATION OF PRESENCE OR ABSENCE OF HISTOPATHOLOGICAL FEATURES AT TIME OF SORTING |
|---|---|
| LARGE INTESTINE LEFT PART | TUBULAR STRUCTURE AND MUCUS PRESENT |
| LARGE INTESTINE LEFT PART | TUBULAR STRUCTURE AND MUCUS LEAKAGE |
| LARGE INTESTINE LEFT PART | RAIL PATTERN |
| LARGE INTESTINE LEFT PART | HIGH-GRADE CELL ATYPIA |
| LARGE INTESTINE LEFT PART | TRABECULAR STRUCTURE AND MUCUS PRESENT |
| LARGE INTESTINE LEFT PART | TRABECULAR STRUCTURE AND MUCUS LEAKAGE |
| LARGE INTESTINE LEFT PART | TUMOR-CELL RATIO LARGER THAN 50% |
| LARGE INTESTINE LEFT PART | SOLID NEST |
| LARGE INTESTINE LEFT PART | SMALL SOLID NEST |
| LARGE INTESTINE LEFT PART | SMALL SOLID NEST AND TYPICAL CELLS |
| LARGE INTESTINE LEFT PART | LARGE SOLID NEST |
| LARGE INTESTINE LEFT PART | LARGE SOLID NEST AND TYPICAL CELLS |
| LARGE INTESTINE LEFT PART | ELONGATED ELLIPTIC NUCLEUS |
| LARGE INTESTINE LEFT PART | PAPILLARY STRUCTURE |
| LARGE INTESTINE LEFT PART | MUCUS PRESENT |
| LARGE INTESTINE LEFT PART | MUCUS LEAKAGE |
| LARGE INTESTINE LEFT PART | NON-SERRATED AND PAPILLARY STRUCTURE |
| LARGE INTESTINE LEFT PART | NON-SERRATED AND PAPILLARY STRUCTURE AND NO MUCUS PRESENT |
| LARGE INTESTINE LEFT PART | NON-SERRATED AND PAPILLARY STRUCTURE AND MUCUS PRESENT |
| LARGE INTESTINE LEFT PART | ROUNDISH NUCLEUS |
| LARGE INTESTINE LEFT PART | CRIBRIFORM STRUCTURE |
| LARGE INTESTINE LEFT PART | CRIBRIFORM STRUCTURE AND NO MUCUS PRESENT |
| LARGE INTESTINE LEFT PART | CRIBRIFORM STRUCTURE AND MUCUS PRESENT |
| LARGE INTESTINE LEFT PART | CRIBRIFORM STRUCTURE AND MUCUS PRESENT |
| LARGE INTESTINE LEFT PART | CRIBRIFORM STRUCTURE AND MUCUS LEAKAGE |
| LARGE INTESTINE LEFT PART | BUDDING PRESENT |

INFORMATION PROCESSING SYSTEM, INFORMATION PROCESSING METHOD, AND PROGRAM

TECHNICAL FIELD

The present invention relates to an information processing system, an information processing method, and a program.

BACKGROUND ART

Regarding cancers, such as lung cancer, colorectal cancer, stomach cancer, breast cancer, gastrointestinal stromal tumor (GIST), and skin cancer (e.g., malignant melanoma), in response to a medical doctor's decision, cancer genetic testing is carried out for examination of one or some genes. Then, diagnosis and treatment with medicine selected based on a test result are carried out (refer to Non Patent Literature 1).

CITATION LIST

Non Patent Literature

Non Patent Literature 1: https://ganjoho.jp/public/dia_tre/treatment/genomic_medicin e/gentest02.html

SUMMARY OF INVENTION

Technical Problem

Because it takes one to two months to obtain a result of cancer genetic testing, administration of medicine effective against the gene abnormality of a patient is delayed. Due to deterioration of the patient's condition during the delay, it is likely to be too late. In particular, such a problem is severe to a stage 4 cancer patient who does not have much time left.

There is a similar problem regarding diseases which are different from cancers and to which medicine effective against gene abnormality can be administrated.

The object of an aspect of the present invention having been made in consideration of the above problems is to provide an information processing system, an information processing method, and a program that enable inhibition of delay of administration of medication effective against the gene abnormality of a target disease.

The object of another aspect of the present invention having been made in consideration of the above problems is to provide an information processing system, an information processing method, and a program that enable inhibition of delay of administration of medication effective against the gene abnormality of a patient having colorectal cancer.

The object of another aspect of the present invention having been made in consideration of the above problems is to provide an information processing system enabling inhibition of delay of administration of medication effective against the gene abnormality of a cancer patient.

Solution to Problem

An information processing system according to a first aspect of the present invention comprises: an acquisition unit configured to acquire a pathologic tissue image of a patient having a target disease; a division unit configured to divide the pathologic tissue image of the patient into a plurality of region images; a feature prediction unit configured to input each of the plurality of region images to each of a plurality of feature prediction models constructed one-to-one for types of histopathological features, to acquire prediction information on presence or absence of the histopathological features; a sorting unit configured to sort a plurality of region images of which respective combinations of presence or absence of the histopathological features based on the acquisition match a previously set combination of presence or absence of the histopathological features at time of sorting; a gene mutation prediction unit configured to input each of the plurality of region images selected by the sorting to each of gene mutation prediction models constructed one-to-one for types of gene mutations, the gene mutation prediction models each having a combination of presence or absence of the histopathological features, to acquire prediction information on presence or absence of the gene mutations; and a prediction result output unit configured to output, with the prediction information on presence or absence of the gene mutations acquired for each region image, a prediction result of presence or absence of at least one gene mutation in the patient.

According to the configuration, input of a pathologic tissue image of a patient having a target disease enables prompt acquisition of a prediction result of the present or absence of gene mutation. Thus, with reference to the prediction result, a clinician can prescribe the patient medication corresponding to the prediction result of the presence or absence of gene mutation, so that administration of medication effective against the gene abnormality of the target disease can be inhibited from being delayed.

An information processing system according to a second aspect of the present invention, according to the first aspect of the information processing system, wherein the acquisition unit further acquires a primary lesion site of the target disease, and the sorting unit sorts the plurality of region images, with the acquired primary lesion site of the target disease together with combinations of presence or absence of the histopathological features based on the acquisition.

According to the configuration, sorting of an region image with the primary lesion site of the target disease leads to a rise in the probability that an region image to be input to a gene mutation prediction model can be limited to an region image relating to the target disease, so that an improvement can be made in the accuracy of prediction of the presence or absence of gene mutation.

An information processing system according to a third aspect of the present invention, according to the first or the second aspect of the information processing system, wherein the plurality of feature prediction models each results from machine learning with learning data including a divided region image of a pathologic tissue image as an input and a histopathological feature given to the divided region image as an output, and the gene mutation prediction models each result from machine learning with learning data including an region image sorted with a combination of presence or absence of the histopathological features as an input and information on presence or absence of a particular gene mutation as an output.

According to the configuration, the feature prediction models and the gene mutation prediction models correspond to models after machine learning, enabling an improvement in the accuracy of prediction of the presence or absence of gene mutation.

An information processing system for predicting a gene having mutated in colorectal cancer tissue of a patient having colorectal cancer, the information processing system comprises: an acquisition unit configured to acquire a colorectal-cancer pathologic tissue image of the patient; a division unit configured to divide the colorectal-cancer pathologic tissue image of the patient into a plurality of region images; a feature prediction unit configured to input each of the plurality of region images to each of a plurality of feature prediction models constructed one-to-one for types of histopathological features, to acquire prediction information on presence or absence of the histopathological features; a sorting unit configured to sort a plurality of region images of which respective combinations of presence or absence of the histopathological features based on the acquisition match a combination of presence or absence of the histopathological features at time of sorting previously set to at least one of BRAF, BRAF V600E, ERBB2, RAS, TP53, or MSI; a gene mutation prediction unit configured to input each of the sorted plurality of region images to each of gene mutation prediction models constructed one-to-one for types of gene mutations, the gene mutation prediction models each having a combination of presence or absence of the histopathological features, to acquire prediction information on presence or absence of the gene mutations; and a prediction result output unit configured to output, with the prediction information on presence or absence of the gene mutations acquired for each region image, a prediction result of presence or absence of at least one gene mutation of BRAF, BRAF V600E, ERBB2, RAS, TP53, or MSI in the patient.

According to the configuration, input of a colorectal-cancer pathologic tissue image of a patient having colorectal cancer enables prompt acquisition of a prediction result of the presence or absence of gene mutation. Thus, with reference to the prediction result, a clinician can prescribe the patient medication corresponding to the prediction result of the presence or absence of gene mutation, so that administration of medication effective against the gene abnormality of the colorectal cancer can be inhibited from being delayed.

An information processing system according to a fifth aspect of the present invention, according to the fourth aspect of the information processing system, wherein the acquisition unit further acquires a primary lesion site of the colorectal cancer, and the sorting unit sorts the plurality of region images, with the acquired primary lesion site of the colorectal cancer together with at least one histopathological feature based on the determination.

According to the configuration, sorting of an region image with the primary lesion site of the target disease leads to a rise in the probability that an region image to be input to a gene mutation prediction model can be limited to an region image relating to the target disease, so that an improvement can be made in the accuracy of prediction of the presence or absence of gene mutation.

An information processing system according to a sixth aspect of the present invention, according to the fourth or fifth aspect of the information processing system, wherein the plurality of feature prediction models each results from machine learning with learning data including a divided region image of a pathologic tissue image as an input and a histopathological feature given to the divided region image as an output, and the gene mutation prediction models each result from machine learning with learning data including an region image sorted with a combination of presence or absence of the histopathological features as an input and information on presence or absence of a particular gene mutation as an output.

According to the configuration, the feature prediction models and the gene mutation prediction models correspond to models after machine learning, enabling an improvement in the accuracy of prediction of the presence or absence of gene mutation.

An information processing method according to a seventh aspect of the present invention, comprises: an acquisition process of acquiring a pathologic tissue image of a patient having a target disease; a division process of dividing the pathologic tissue image of the patient into a plurality of region images; a feature prediction process of inputting each of the plurality of region images to each of a plurality of feature prediction models constructed one-to-one for types of histopathological features, to acquire prediction information on presence or absence of the histopathological features; a sorting process of sorting a plurality of region images of which respective combinations of presence or absence of the histopathological features based on the acquisition match a previously set combination of presence or absence of the histopathological features at time of sorting; a gene mutation prediction process of inputting each of the plurality of region images selected by the sorting to each of gene mutation prediction models constructed one-to-one for types of gene mutations, the gene mutation prediction models each having a combination of presence or absence of the histopathological features, to acquire prediction information on presence or absence of the gene mutations; and a prediction result output process of outputting, with the prediction information on presence or absence of the gene mutations acquired for each region image, a prediction result of presence or absence of at least one gene mutation in the patient. an acquisition process of acquiring a pathologic tissue image of a patient having a target disease; a division process of dividing the pathologic tissue image of the patient into a plurality of region images; a feature prediction process of inputting each of the plurality of region images to each of a plurality of feature prediction models constructed one-to-one for types of histopathological features, to acquire prediction information on presence or absence of the histopathological features; a sorting process of sorting a plurality of region images of which respective combinations of presence or absence of the histopathological features based on the acquisition match a previously set combination of presence or absence of the histopathological features at time of sorting; a gene mutation prediction process of inputting each of the plurality of region images selected by the sorting to each of gene mutation prediction models constructed one-to-one for types of gene mutations, the gene mutation prediction models each having a combination of presence or absence of the histopathological features, to acquire prediction information on presence or absence of the gene mutations; and a prediction result output process of outputting, with the prediction information on presence or absence of the gene mutations acquired for each region image, a prediction result of presence or absence of at least one gene mutation in the patient.

According to the configuration, input of a pathologic tissue image of a patient having a target disease enables prompt acquisition of a prediction result of the present or absence of gene mutation. Thus, with reference to the prediction result, a clinician can prescribe the patient medication corresponding to the prediction result of the presence or absence of gene mutation, so that administration of medication effective against the gene abnormality of the target disease can be inhibited from being delayed.

An information processing method according to an eighth aspect of the present invention, for predicting a gene having mutated in colorectal cancer tissue of a patient having colorectal cancer, the information processing method comprises: an acquisition process of acquiring a colorectal-cancer pathologic tissue image of the patient; a division process of dividing the colorectal-cancer pathologic tissue image of the patient into a plurality of region images; a feature prediction process of inputting each of the plurality of region images to each of a plurality of feature prediction models constructed one-to-one for types of histopathological features, to acquire prediction information on presence or absence of the histopathological features; a sorting process of sorting a plurality of region images of which respective combinations of presence or absence of the histopathological features based on the acquisition match a combination of presence or absence of the histopathological features at time of sorting previously set to at least one of BRAF, BRAF V600E, ERBB2, RAS, TP53, or MSI; a gene mutation prediction process of inputting each of the sorted plurality of region images to each of gene mutation prediction models constructed one-to-one for types of gene mutations, the gene mutation prediction models each having a combination of presence or absence of the histopathological features, to acquire prediction information on presence or absence of the gene mutations; and a prediction result output process of outputting, with the prediction information on presence or absence of the gene mutations acquired for each region image, a prediction result of presence or absence of at least one gene mutation of BRAF, BRAF V600E, ERBB2, RAS, TP53, or MSI in the patient.

According to the configuration, input of a colorectal-cancer pathologic tissue image of a patient having colorectal cancer enables prompt acquisition of a prediction result of the presence or absence of gene mutation. Thus, with reference to the prediction result, a clinician can prescribe the patient medication corresponding to the prediction result of the presence or absence of gene mutation, so that administration of medication effective against the gene abnormality of the colorectal cancer can be inhibited from being delayed.

A program according to a ninth aspect of the present invention, for causing a computer to carry out: an acquisition process of acquiring a pathologic tissue image of a patient having a target disease; a division process of dividing the pathologic tissue image of the patient into a plurality of region images; a feature prediction process of inputting each of the plurality of region images to each of a plurality of feature prediction models constructed one-to-one for types of histopathological features, to acquire prediction information on presence or absence of the histopathological features; a sorting process of sorting a plurality of region images of which respective combinations of presence or absence of the histopathological features based on the acquisition match a previously set combination of presence or absence of the histopathological features at time of sorting; a gene mutation prediction process of inputting each of the plurality of region images selected by the sorting to each of gene mutation prediction models constructed one-to-one for types of gene mutations, the gene mutation prediction models each having a combination of presence or absence of the histopathological features, to acquire prediction information on presence or absence of the gene mutations; and a prediction result output process of outputting, with the prediction information on presence or absence of the gene mutations acquired for each region image, a prediction result of presence or absence of at least one gene mutation in the patient.

According to the configuration, input of a pathologic tissue image of a patient having a target disease enables prompt acquisition of a prediction result of the present or absence of gene mutation. Thus, with reference to the prediction result, a clinician can prescribe the patient medication corresponding to the prediction result of the presence or absence of gene mutation, so that administration of medication effective against the gene abnormality of the target disease can be inhibited from being delayed.

A program according to a tenth aspect of the present invention, for predicting a gene having mutated in colorectal cancer tissue of a patient having colorectal cancer, the program causing a computer to carry out: an acquisition process of acquiring a colorectal-cancer pathologic tissue image of the patient; a division process of dividing the colorectal-cancer pathologic tissue image of the patient into a plurality of region images; a feature prediction process of inputting each of the plurality of region images to each of a plurality of feature prediction models constructed one-to-one for types of histopathological features, to acquire prediction information on presence or absence of the histopathological features; a sorting process of sorting a plurality of region images of which respective combinations of presence or absence of the histopathological features based on the acquisition match a combination of presence or absence of the histopathological features at time of sorting previously set to at least one of BRAF, BRAF V600E, ERBB2, RAS, TP53, or MSI; a gene mutation prediction process of inputting each of the sorted plurality of region images to each of gene mutation prediction models constructed one-to-one for types of gene mutations, the gene mutation prediction models each having a combination of presence or absence of the histopathological features, to acquire prediction information on presence or absence of the gene mutations; and a prediction result output process of outputting, with the prediction information on presence or absence of the gene mutations acquired for each region image, a prediction result of presence or absence of at least one gene mutation of BRAF, BRAF V600E, ERBB2, RAS, TP53, or MSI in the patient.

According to the configuration, input of a colorectal-cancer pathologic tissue image of a patient having colorectal cancer enables prompt acquisition of a prediction result of the presence or absence of gene mutation. Thus, with reference to the prediction result, a clinician can prescribe the patient medication corresponding to the prediction result of the presence or absence of gene mutation, so that administration of medication effective against the gene abnormality of the colorectal cancer can be inhibited from being delayed.

An information processing system according to an eleven th aspect of the present invention, for estimating presence or absence of BRAF gene mutation in a tumor, the information processing system comprising: means of dividing a pathologic tissue image of the tumor into one or a plurality of images; means of selecting, from among the divided images, at least one image of an image having a tumor-cell ratio larger than 50%, an image including a papillary structure, an image including a non-serrated and papillary structure, an image including a non-serrated and papillary structure and mucus present, an image including a cribriform structure, an image including a cribriform structure and no mucus present, or an image including a cribriform structure and mucus present; and means of estimating, with the selected at least one image, the presence or absence of the BRAF gene mutation.

According to the configuration, input of a pathologic tissue image enables prompt acquisition of a prediction result of the presence or absence of the BRAF gene mutation. Thus, with reference to the prediction result, a clinician can prescribe the patient medication corresponding to the prediction result of the presence or absence of the BRAF gene mutation, so that administration of medication effective against the BRAF gene abnormality of cancer can be inhibited from being delayed.

An information processing system according to a twelfth aspect of the present invention, for estimating presence or absence of BRAF V600E gene mutation in a tumor, the information processing system comprises: means of dividing a pathologic tissue image of the tumor into one or a plurality of images; means of selecting, from among the divided images, at least one image of an image including a rail pattern, an image including a small solid nest, an image including a small solid nest of typical cells, an image including a large solid nest of typical cells, an image including an elongated elliptic nucleus, an image including mucus present, an image including a non-serrated and papillary structure and no mucus present, an image including a cribriform structure and no mucus present, or an image including a cribriform structure and mucus present; and means of estimating, with the selected at least one image, the presence or absence of the BRAF V600E gene mutation.

According to the configuration, input of a pathologic tissue image enables prompt acquisition of a prediction result of the presence or absence of the BRAF V600E gene mutation. Thus, with reference to the prediction result, a clinician can prescribe the patient medication corresponding to the prediction result of the presence or absence of the BRAF V600E gene mutation, so that administration of medication effective against the BRAF V600E gene abnormality of cancer can be inhibited from being delayed.

An information processing system according to a thirteenth aspect of the present invention, for estimating presence or absence of ERBB2 gene mutation in a tumor, the information processing system comprises: means of dividing a pathologic tissue image of the tumor into one or a plurality of images; means of selecting, from among the divided images, at least one image of an image including a trabecular structure and mucus present or an image including a trabecular structure and mucus leakage; and means of estimating, with the selected at least one image as an analysis target, the presence or absence of the ERBB2 gene mutation.

According to the configuration, input of a pathologic tissue image enables prompt acquisition of a prediction result of the presence or absence of the ERBB2 gene mutation. Thus, with reference to the prediction result, a clinician can prescribe the patient medication corresponding to the prediction result of the presence or absence of the ERBB2 gene mutation, so that administration of medication effective against the ERBB2 gene abnormality of cancer can be inhibited from being delayed.

An information processing system according to a fourteenth aspect of the present invention, for estimating presence or absence of TP53 gene mutation in a tumor, the information processing system comprises: means of dividing a pathologic tissue image of the tumor into one or a plurality of images; means of selecting, from among the divided images, at least one image of an image including a signet ring cell and mucus leakage, an image including a germ cell, an image including a trabecular structure and no mucus present, or an image including mucus leakage; and means of estimating, with the selected at least one image, the presence or absence of the TP53 gene mutation.

According to the configuration, input of a pathologic tissue image enables prompt acquisition of a prediction result of the presence or absence of the TP53 gene mutation. Thus, with reference to the prediction result, a clinician can prescribe the patient medication corresponding to the prediction result of the presence or absence of the TP53 gene mutation, so that administration of medication effective against the TP53 gene abnormality of cancer can be inhibited from being delayed.

An information processing system according to a fifteenth aspect of the present invention, for estimating presence or absence of MSI gene abnormality in a tumor, the information processing system comprises: means of dividing a pathologic tissue image of the tumor into one or a plurality of images; means of selecting, from among the divided images, at least one image of an image including a rail pattern, an image including a trabecular structure and no mucus present, an image having a tumor-cell ratio larger than 50%, an image including a solid nest, an image including a small solid nest of typical cells, an image including an elongated elliptic nucleus, an image including a papillary structure, an image including a germ cell, an image including a non-serrated and papillary structure, an image including a roundish nucleus, an image including a cribriform structure and no mucus present, an image including a cribriform structure and mucus present, or an image including a cribriform structure and mucus leakage; and means of estimating, with the selected at least one image, the presence or absence of the MSI gene abnormality.

According to the configuration, input of a pathologic tissue image enables prompt acquisition of a prediction result of the presence or absence of the MSI gene abnormality. Thus, with reference to the prediction result, a clinician can prescribe the patient medication corresponding to the prediction result of the presence or absence of the MSI gene abnormality, so that administration of medication effective against the MSI gene abnormality of cancer can be inhibited from being delayed.

An information processing system according to a sixteenth aspect of the present invention, for estimating presence or absence of RAS gene mutation in a tumor, the information processing system comprising: means of dividing a pathologic tissue image of the tumor into one or a plurality of images; means of selecting, from among the divided images, at least one image of an image including a signet ring cell and mucus leakage, an image including a tubular structure and no mucus present, an image including a trabecular structure and no mucus present, an image including a small solid nest, an image including a large solid nest, an image including a large solid nest of typical cells, an image including a papillary structure, an image including no mucus present, an image including mucus present, an image including a germ cell, an image including a non-serrated and papillary structure, an image including a non-serrated and papillary structure and no mucus present, an image including a non-serrated and papillary structure and mucus present, an image including a cribriform structure, an image including a cribriform structure and no mucus present, an image including a cribriform structure and mucus present, an image including a cribriform structure and mucus leakage, an image including budding present, an image having a tumor-cell ratio larger than 50%, an image including a small solid nest, an image including a small solid nest of typical cells, an image including a large solid nest, an image including an elongated elliptic nucleus, an image including mucus present, an image including mucus leakage, an image including a non-serrated and papillary structure and no mucus present, an image including a cribriform structure, an image including a cribriform structure and no mucus present, an image including a cribriform structure and mucus present, an image including a tubular structure and mucus present, an image including a tubular structure and mucus leakage, an image including a rail pattern, an image including a high-grade cell atypia, an image including a trabecular structure and mucus present, an image including a trabecular structure and mucus leakage, an image including a solid nest, an image including a non-serrated and papillary structure, an image including a non-serrated and papillary structure and mucus present, or an image including a roundish nucleus; and means of estimating, with the selected at least one image, the presence or absence of the RAS gene mutation.

According to the configuration, input of a pathologic tissue image enables prompt acquisition of a prediction result of the presence or absence of the RAS gene mutation. Thus, with reference to the prediction result, a clinician can prescribe the patient medication corresponding to the prediction result of the presence or absence of the RAS gene mutation, so that administration of medication effective against the RAS gene abnormality of cancer can be inhibited from being delayed.

Advantageous Effects of Invention

According to the configuration, input of a pathologic tissue image of a patient having a target disease enables prompt acquisition of a prediction result of the present or absence of gene mutation. Thus, with reference to the prediction result, a clinician can prescribe the patient medication corresponding to the prediction result of the presence or absence of gene mutation, so that administration of medication effective against the gene abnormality of the target disease can be inhibited from being delayed.

According to another aspect of the present invention, input of a colorectal-cancer pathologic tissue image of a patient having colorectal cancer enables prompt acquisition of a prediction result of the presence or absence of gene mutation. Thus, with reference to the prediction result, a clinician can prescribe the patient medication corresponding to the prediction result of the presence or absence of gene mutation, so that administration of medication effective against the gene abnormality of the colorectal cancer can be inhibited from being delayed.

BRIEF DESCRIPTION OF DRAWINGS

FIG. 9 illustrates, in a case where the target gene mutation is BRAF+, a set of the sorted primary lesion site and the combination of the presence or absence of the histopathological features at the time of sorting.

FIG. 10 illustrates, in a case where the target gene mutation is BRAF V600E+, a set of the sorted primary lesion site and the combination of the presence or absence of the histopathological features at the time of sorting.

FIG. 11 illustrates, in a case where the target gene mutation is ERBB2+, a set of the sorted primary lesion site and the combination of the presence or absence of the histopathological features at the time of sorting.

FIG. 12 illustrates, in a case where the target gene mutation is TP53+, a set of the sorted primary lesion site and the combination of the presence or absence of the histopathological features at the time of sorting.

FIG. 13 illustrates, in a case where the state of gene abnormality is MSI, a set of the sorted primary lesion site and the combination of the presence or absence of the histopathological features at the time of sorting.

FIG. 14 illustrates, in a case where the target gene mutation is RAS+, a set of the sorted primary lesion site and the combination of the presence or absence of the histopathological features at the time of sorting.

FIG. 15 follows FIG. 14.

FIG. 16 illustrates exemplary tables stored in the storage 23.

FIG. 17 follows FIG. 16.

DESCRIPTION OF EMBODIMENTS

Embodiments will be described below with reference to the drawings. Note that detailed description more than necessary will be omitted. For example, detailed description of already well-known matters or duplicate description of substantially identical configurations will be omitted. This is for avoidance of redundant description in the following and for those skilled in the art to have easy understanding.

Examples of a target disease to be subjected to prediction of the presence or absence of gene mutation according to the present embodiment include diseases with gene mutation in tissue, such as cancers (or diseases to which medicine effective against gene abnormality can be administrated). As an exemplary target disease according to the present embodiment, colorectal cancer will be given in the following description. Note that, in the present embodiment, as description, gene abnormality is included in gene mutation.

Figure 1:
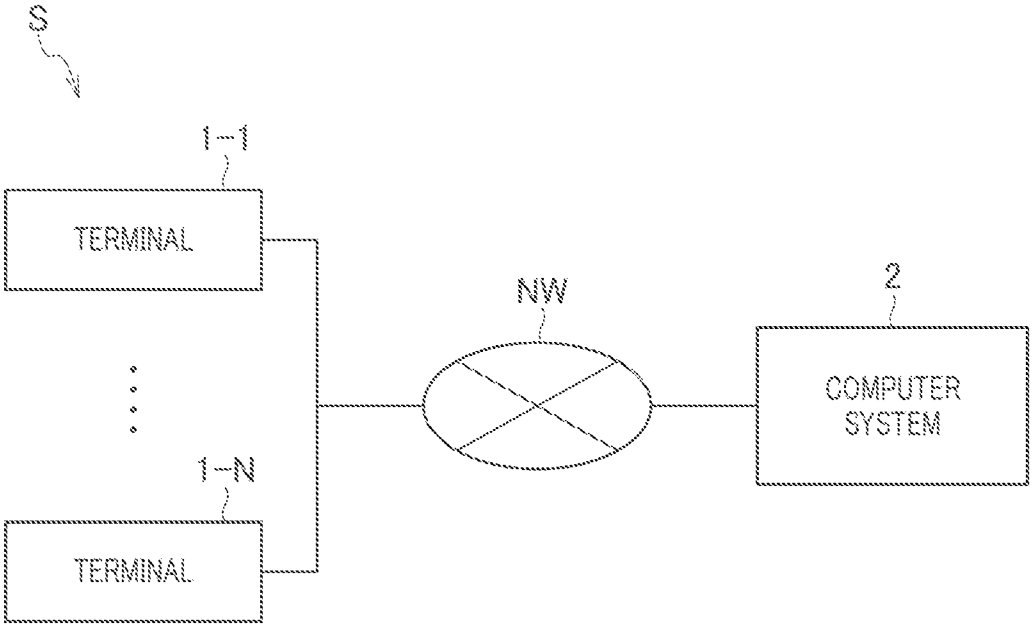
FIG. 1 is a schematic diagram of the configuration of an information processing system according to the present embodiment.

FIG. 1 is a schematic diagram of the configuration of an information processing system according to the present embodiment. As illustrated in FIG. 1, the information processing system S includes terminals 1-1 to 1-N(N is a natural number) and a computer system 2 connected thereto through a communication circuit network NW.

The terminals 1-1 to 1-N are to be used by different users and are each, for example, a mobile phone, such as a multifunctional mobile phone (so-called smartphone), a tablet, a laptop personal computer, or a desktop personal computer. For example, the terminals 1-1 to 1-N may each display, through a WEB browser, information transmitted from the computer system 2 or may display, on the respective screens of applications installed on the terminals 1-1 to 1-N, information transmitted from the computer system 2. An example in which the terminals 1-1 to 1-N each display, through a WEB browser, information transmitted from the computer system 2 will be given in the following description.

The computer system 2 is capable of communicating with the terminals 1-1 to 1-N, and such communications may be made by wire or by wireless. That is, the computer system 2 is connected to the terminals 1-1 to 1-N such that information can be exchanged. For example, the computer system 2 is used by an administrator who manages the information processing system S according to the present embodiment. The computer system 2 may be a single computer or may include a plurality of computers.

Figure 2:
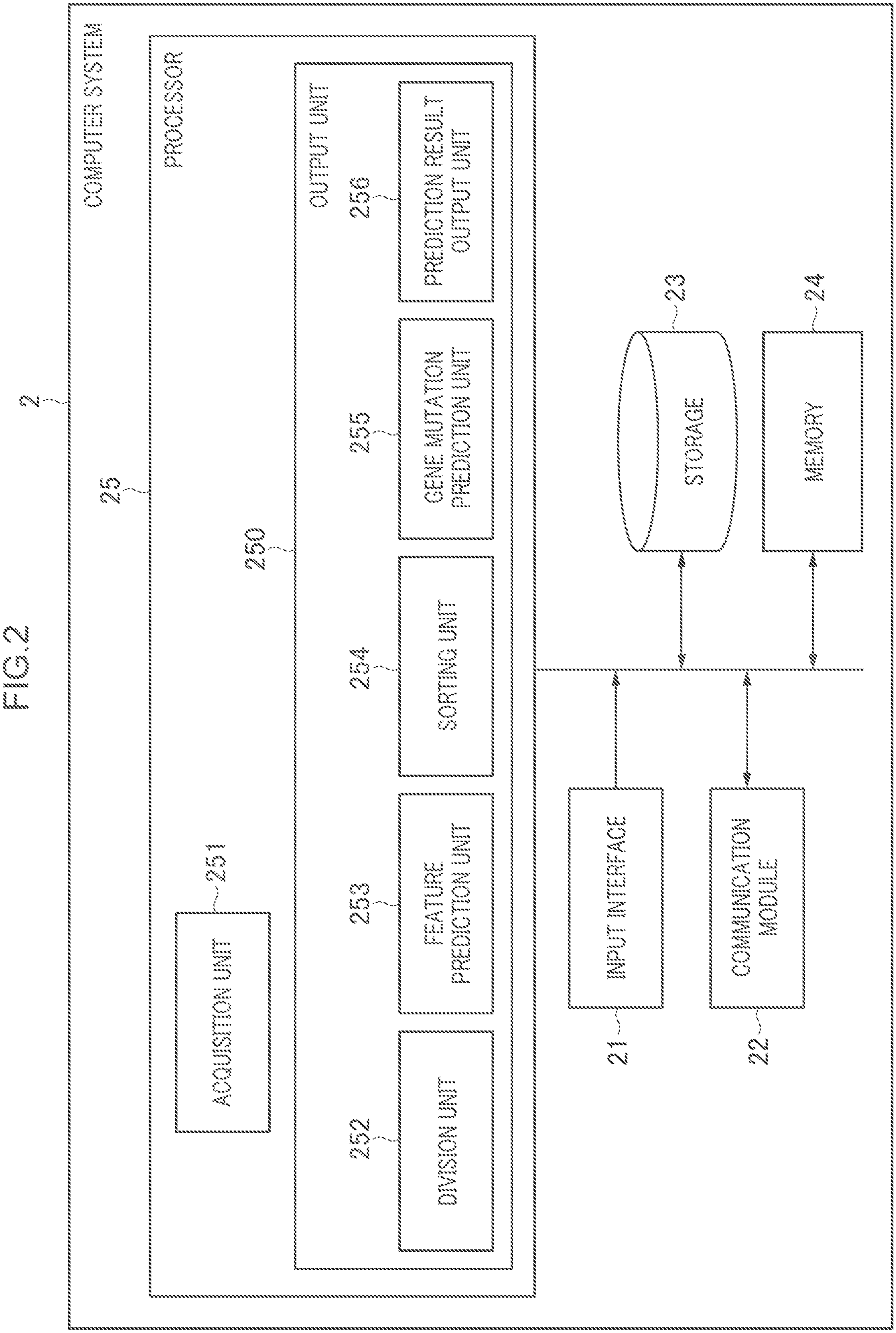
FIG. 2 is a schematic diagram of the configuration of the computer system according to the present embodiment.

FIG. 2 is a schematic diagram of the configuration of the computer system according to the present embodiment. As illustrated in FIG. 2, the computer system 2 includes an input interface 21, a communication module 22, a storage 23, a memory 24, and a processor 25.

The input interface 21 receives an input from the administrator of the computer system 2 and outputs an input signal corresponding to the received input to the processor 25.

The communication module 22 is connected to the communication circuit network NW and communicates with the terminals 1-1 to 1-N. Such communications may be made by wire or by wireless. In the following description, such communications are made by wire.

The storage 23 stores a program that the processor 25 reads out and executes, a feature prediction model after machine learning, a mutation prediction model after machine learning, and various types of data.

The memory 24 temporarily retains data and a program. The memory 24 is a volatile memory and serves, for example, as a random access memory (RAM).

The processor 25 loads a program from the storage 23 to the memory 24 and executes a series of commands included in the program, to function as an acquisition unit 251 and an output unit 250. The output unit 250 has, for example, a division unit 252, a feature prediction unit 253, a sorting unit 254, a gene mutation prediction unit 255, and a prediction result output unit 256. Respective pieces of processing thereof will be described below.

Figure 3:
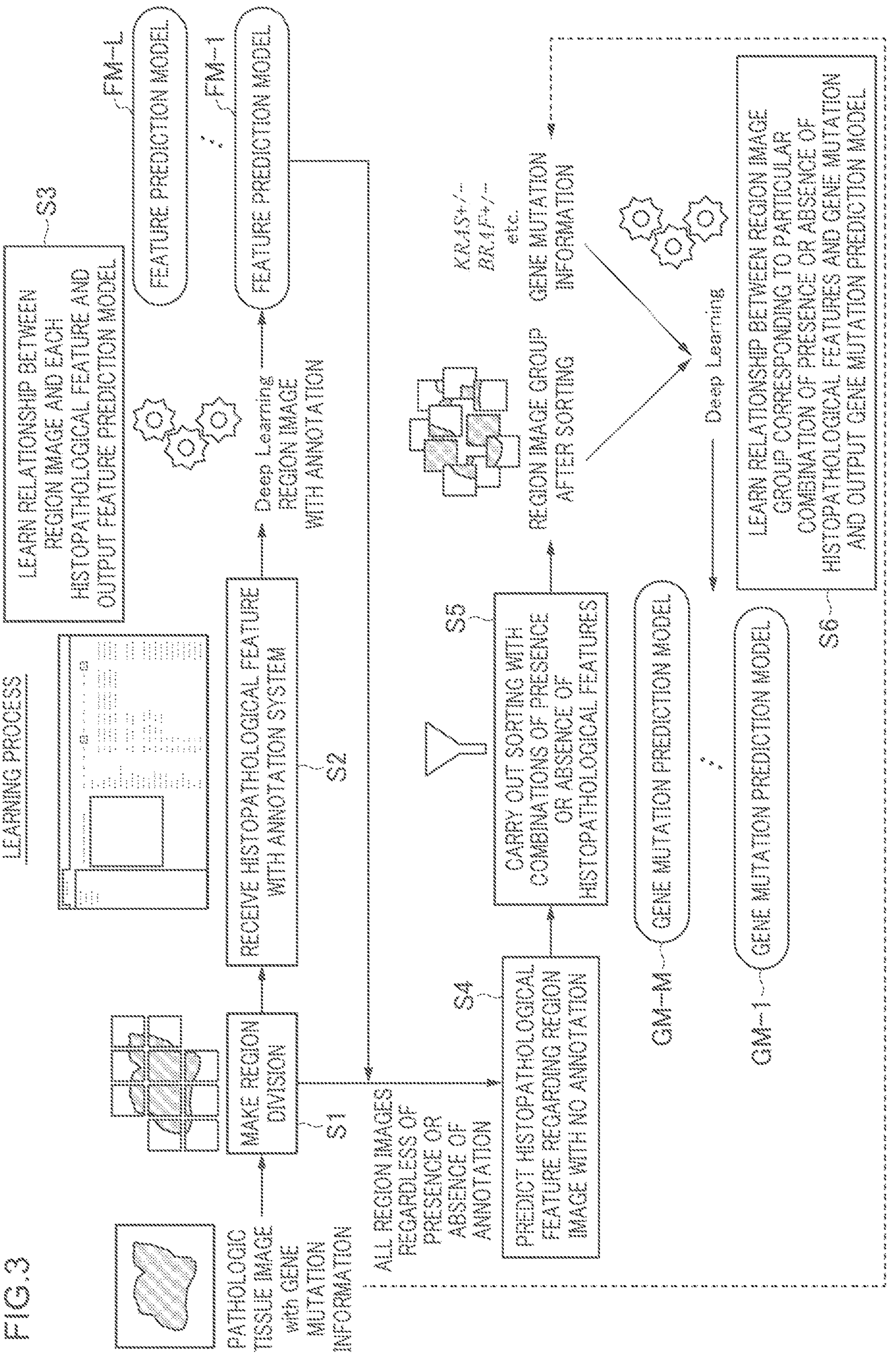
FIG. 3 is a schematic diagram of a learning process for a gene mutation prediction model.

Next, a learning process for a gene mutation prediction model will be described with FIG. 3. FIG. 3 is a schematic diagram of a learning process for a gene mutation prediction model.

(Step S1) The division unit 252 divides, into one or a plurality of region images (e.g., tiled images shaped like tiles), an image (e.g., a slide image) of the pathologic tissue (herein, colorectal cancer tissue as an example) of a patient having a target disease (herein, colorectal cancer as an example). Here, the gene mutation of the disease tissue (herein, colorectal cancer tissue as an example) of the patient has been known. Here, division into tiled images shaped like tiles is also referred to as tiling division.

(Step S2) Subsequently, for example, with an annotation system, a pathologist inputs a histopathological feature (e.g., elongated elliptic nucleus) regarding each of the plurality of region images. At the time, a terminal device (not illustrated) used by the pathologist receives the histopathological feature. The acquisition unit 251 acquires the histopathological feature given for each of the plurality of region images.

(Step S3) Subsequently, per histopathological feature, the processor 25 learns the relationship between an region image and the histopathological feature and outputs a feature prediction model. Specifically, for example, with learning data including a divided region image of the pathologic tissue image as an input and the histopathological feature given to the region image as an output, the processor 25 learns by machine learning (e.g., deep learning) and then outputs a feature prediction model. Thus, feature prediction models, of which the number is identical to the number of histopathological features L (L is a natural number), are output, so that the feature prediction models FM-1 to FM-L are stored in the storage 23 by the processor 25. Such a feature prediction model as above results from machine learning with learning data including a divided region image of the pathologic tissue image as an input and the histopathological feature given to the region image as an output.

(Step S4) Next, with the feature prediction models FM-1 to FM-L, the processor 25 predicts the presence or absence of each histopathological feature regarding a divided image (herein, a tiled image as an example) to which no histopathological feature is annotated. Thus, the presence or absence of each histopathological feature is predicted to the divided image to which no histopathological feature is annotated.

(Step S5) Next, with the combinations of the presence or absence of the histopathological features predicted, the sorting unit 254 sorts an region image (herein, a tiled image as an example) from the plurality of region images. Specifically, with the histopathological features predicted in step S4, the sorting unit 254 extracts an region image (herein, a tiled image as an example) corresponding to a particular combination of the presence or absence of the histopathological features.

(Step S6) Next, the processor 25 learns the relationship between a tiled image group corresponding to the particular combination of the presence or absence of the histopathological features and gene mutation and then outputs a gene mutation prediction model. Specifically, for example, with learning data including an region image corresponding to the particular combination of the presence or absence of the histopathological features (region image extracted in step S5) as an input and information on the presence or absence of a particular gene mutation as an output, the processor 25 learns by machine learning (e.g., deep learning) and outputs a gene mutation prediction model. Thus, gene mutation prediction models, of which the number is identical to the number of gene mutations M (M is a natural number), are output, so that the gene mutation prediction models GM-1 to GM-M are stored in the storage 23 by the processor 25. Such a gene mutation prediction model as above results from machine learning with learning data including an region image sorted with a particular combination of the presence or absence of the histopathological features as an input and information on the particular gene mutation as an output.

Figure 4A:
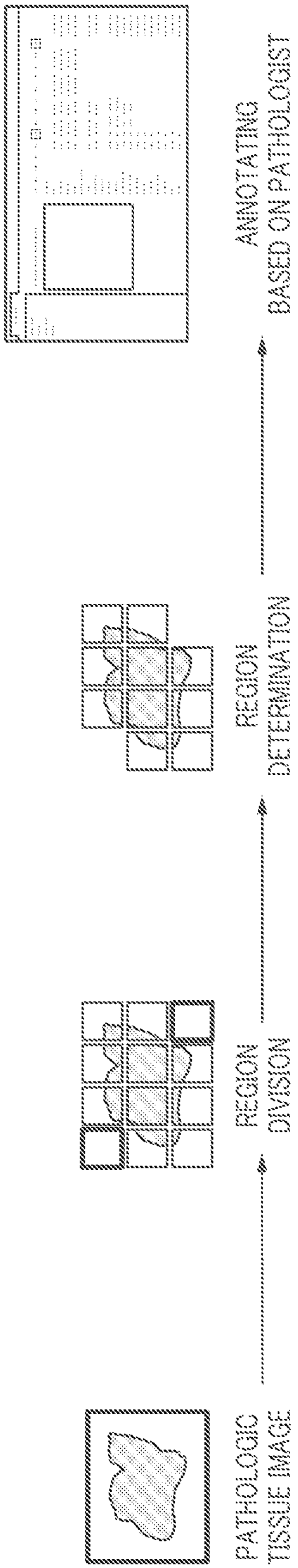
FIG. 4A is a schematic diagram for describing a process of annotating a histopathological feature to a pathologic tissue image.

Next, a process of annotating a histopathological feature to a pathologic tissue image will be described with FIGS. 4A and 4B. FIG. 4A is a schematic diagram for describing a process of annotating a histopathological feature to a pathologic tissue image. As illustrated in FIG. 4A, a pathologic tissue image is divided into a plurality of region images.

From among the generated region images, an region image including no cellular tissue (hereinafter, also referred to as a white image) and an region image in which matter different from the cellular tissue (e.g., magic ink) is larger in amount than the criterion are excluded. Such processing is referred to as region determination. The region images not excluded are each annotated manually (e.g., by a pathologist) with a histopathological feature.

Figure 4B:
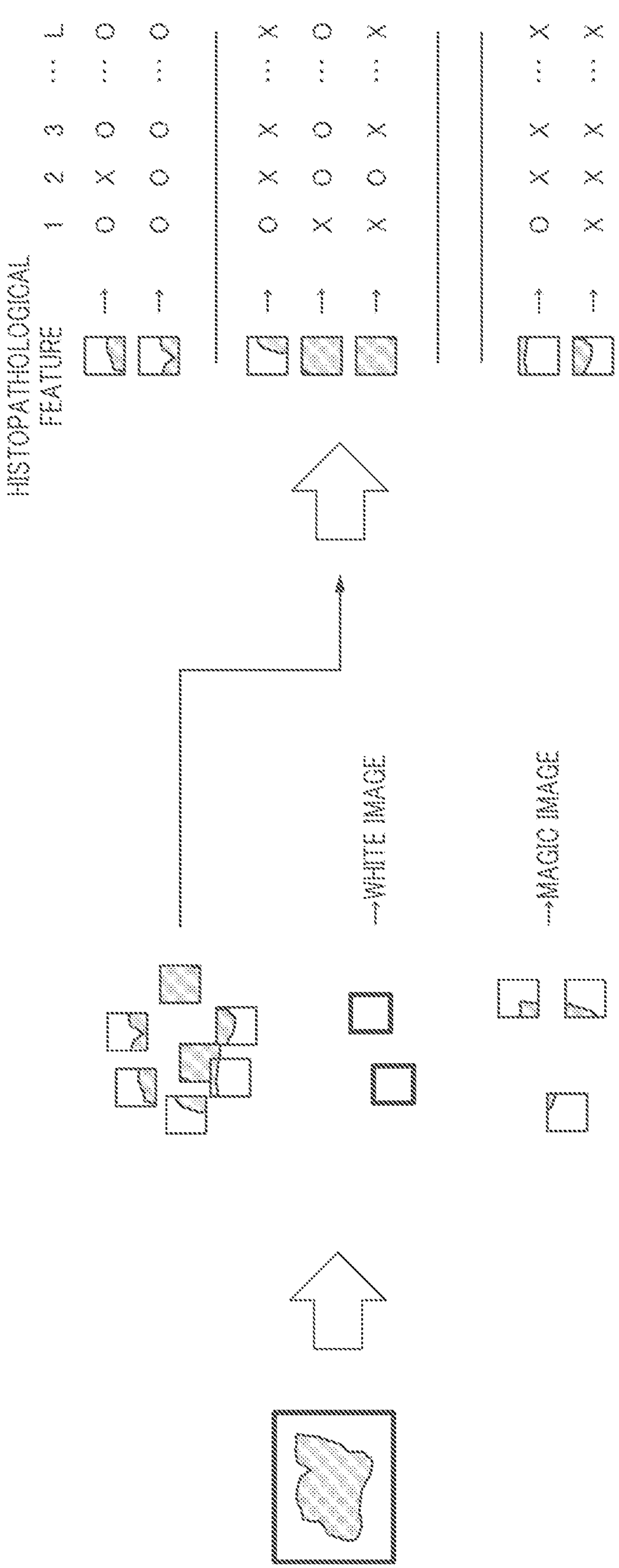
FIG. 4B is a schematic diagram of an exemplary process of annotating a histopathological feature to a pathologic tissue image.

FIG. 4B is a schematic diagram of an exemplary process of annotating a histopathological feature to a pathologic tissue image. As illustrated in FIG. 4B, a pathologic tissue image is divided into a plurality of region images. From among the region images, a white image and an region image including magic ink larger in amount than the criterion (also referred to as a magic image) are excluded. The region images not excluded are each given the presence or absence of each histopathological feature. Referring to FIG. 4B, ○ indicates the presence of a histopathological feature and x indicates the absence of a histopathological feature. The region images are each given the presence or absence of each of L number of histopathological features.

Figure 5:
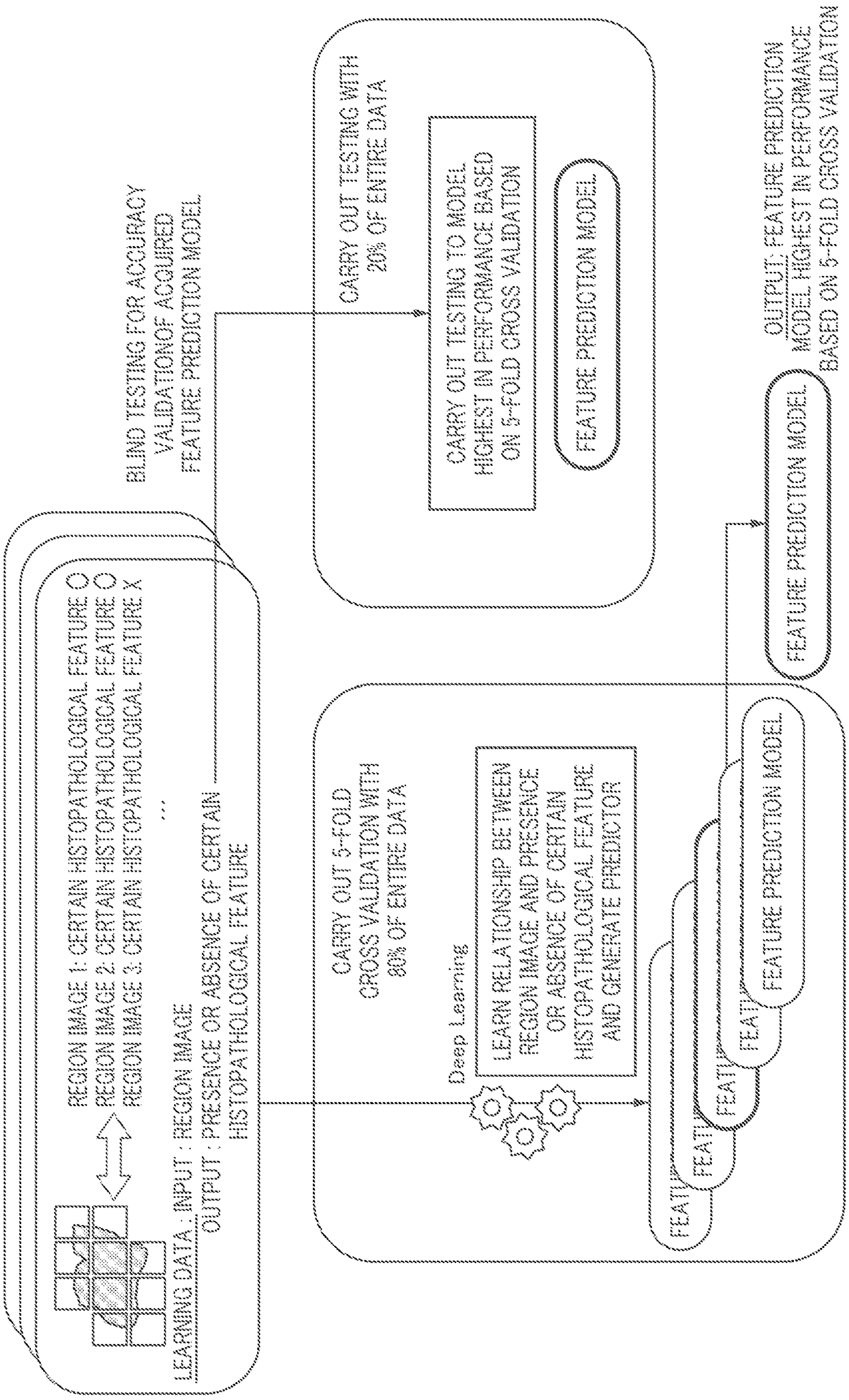
FIG. 5 is a schematic diagram for describing learning and testing at the time of construction of a feature prediction model for a certain histopathological feature.

Next, learning and testing at the time of construction of a feature prediction model for a certain histopathological feature will be described with FIG. 5. FIG. 5 is a schematic diagram for describing learning and testing at the time of construction of a feature prediction model for a certain histopathological feature. As illustrated in FIG. 5, learning data includes a set of an region image and the presence or absence of a certain histopathological feature. Machine learning is carried out with the region image given to the input of a machine learning model and the presence or absence of the certain histopathological feature given to the output of the machine learning model. Thus, learning of the relationship between the region image and the presence or absence of the certain histopathological feature causes generation of a feature prediction model for predicting the certain histopathological feature.

As an example, at the time of learning, 5-fold cross validation is carried out with 80% of the entire learning data. That is, learning is carried out with 64% of the entire learning data and validation is carried out with 16% of the entire learning data. Specifically, validation is carried out as follows. First, 80% of the entire learning data is divided into five. Here, for easy understanding, subsets of data resulting from the division into five are defined as s1, s2, s3, s4, and s5.

For example, after 80% of the learning data is divided into five, first, with the subsets s1, s2, s3, and s4 as training subsets, model learning starts. Subsequently, with s5 as a validation subset, model validation is carried out. The evaluation indicator acquired at the time (e.g., accuracy or F1 score) is defined as el.

Next, learning is carried out with s2, s3, s4, and s5 and evaluation is carried out with s1. Similarly, learning and evaluation are repeated with replacement of the subsets. Learning and evaluation are repeated to all the combinations, so that five evaluation indicators are acquired. Then, the model highest in performance based on the five evaluation indicators is determined as a feature prediction model.

For accuracy validation of the acquired feature prediction model, with 20% of the entire learning data, blind testing is carried out to the model highest in performance based on the 5-fold cross validation. Thus, the performance of the determined feature prediction model is validated, and the feature prediction model is adopted if its performance fulfills the criterion.

Figure 6A:
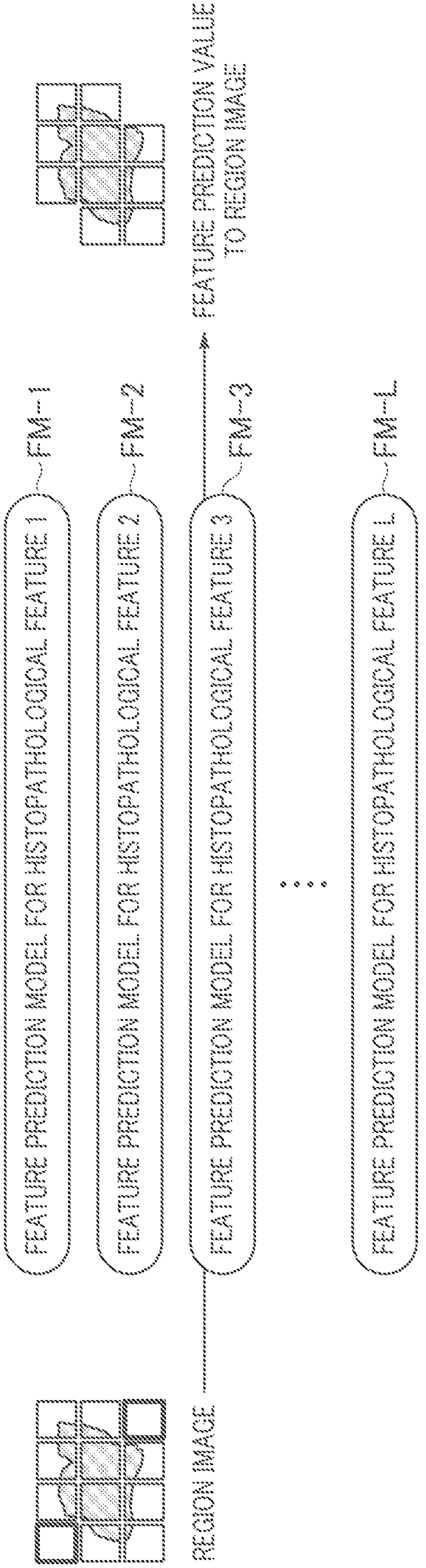
FIG. 6A is a schematic diagram for describing giving the prediction value of a histopathological feature to an region image.

Next, giving the prediction value of a histopathological feature to an region image in step S4 of FIG. 3 will be described with FIGS. 6A and 6B. FIG. 6A is a schematic diagram for describing giving the prediction value of a histopathological feature to an region image. FIG. 6A illustrates the feature prediction model FM-1 for a histopathological feature 1, the feature prediction model FM-2 for a histopathological feature 2, and the feature prediction model FM-3 for a histopathological feature 3 to the feature prediction model FM-L for a histopathological feature L.

The prediction value of a histopathological feature corresponds to the degree of the histopathological feature determined based on a prediction result from each of the feature prediction models FM-1 to FM-L to each region image. The prediction value of a histopathological feature may be a prediction result itself (e.g., a numerical value of 0 to 1) or may be a value (e.g., the value of 0 or 1) corresponding to a comparison result from comparison of whether a prediction result is larger or smaller than the threshold. An example in which the prediction value of a histopathological feature is a numerical value of 0 to 1 will be given herein.

Figure 6B:
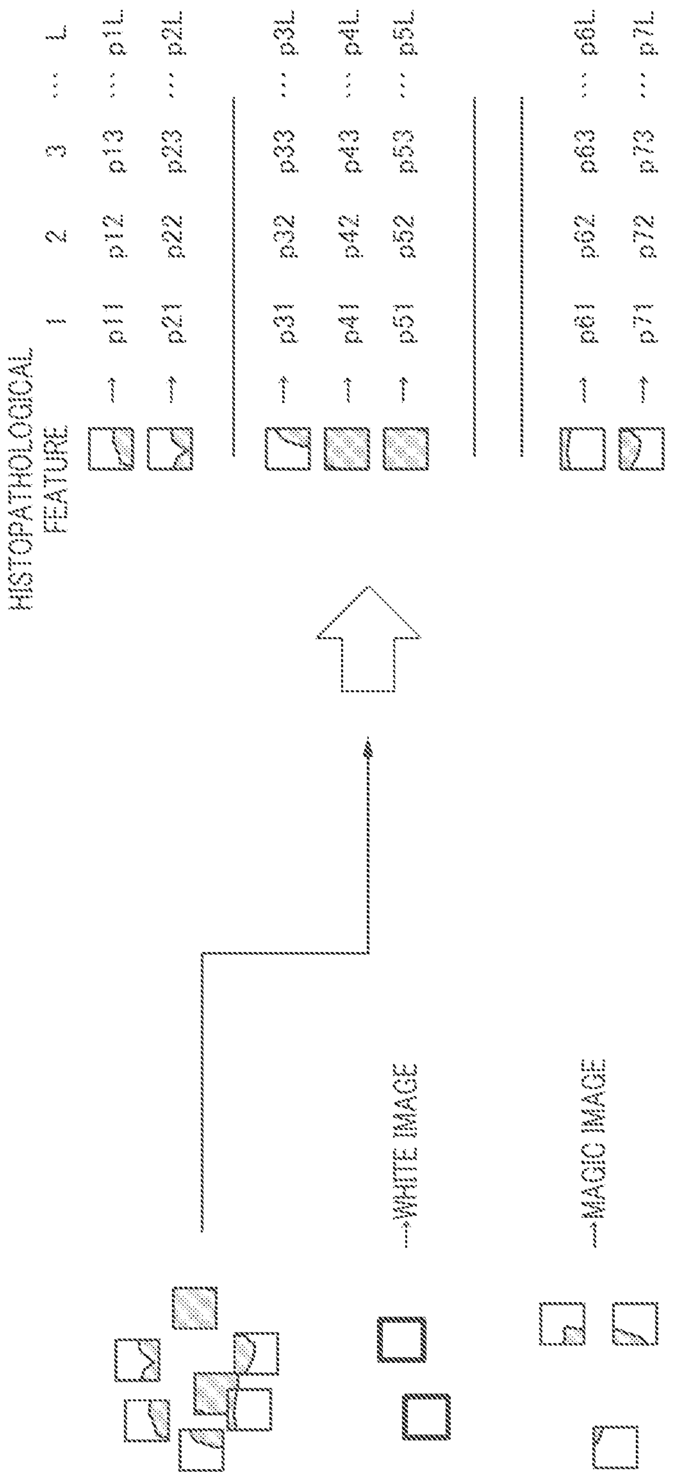
FIG. 6B is a schematic diagram for describing exemplary giving of the prediction value of a histopathological feature to an region image.

FIG. 6B is a schematic diagram for describing exemplary giving of the prediction value of a histopathological feature to an region image. As indicated with feature prediction values p11, p12, p13, . . . , p1L, . . . , p71, p72, p73, . . . p7L in FIG. 6B, each of the region images excluding white images and magic images is given the respective feature prediction values of the histopathological features 1 to L. In this case, in step S5 of FIG. 3, the processor 25 may determine, in a case where a feature prediction value is larger than the threshold, the presence of the histopathological feature thereof and may determine, in a case where a feature prediction value is not more than the threshold, the absence of the histopathological feature thereof. The threshold may be set at a different value or the same value per histopathological feature. Herein, an example in which a different value is set per histopathological feature will be given.

Figure 7:
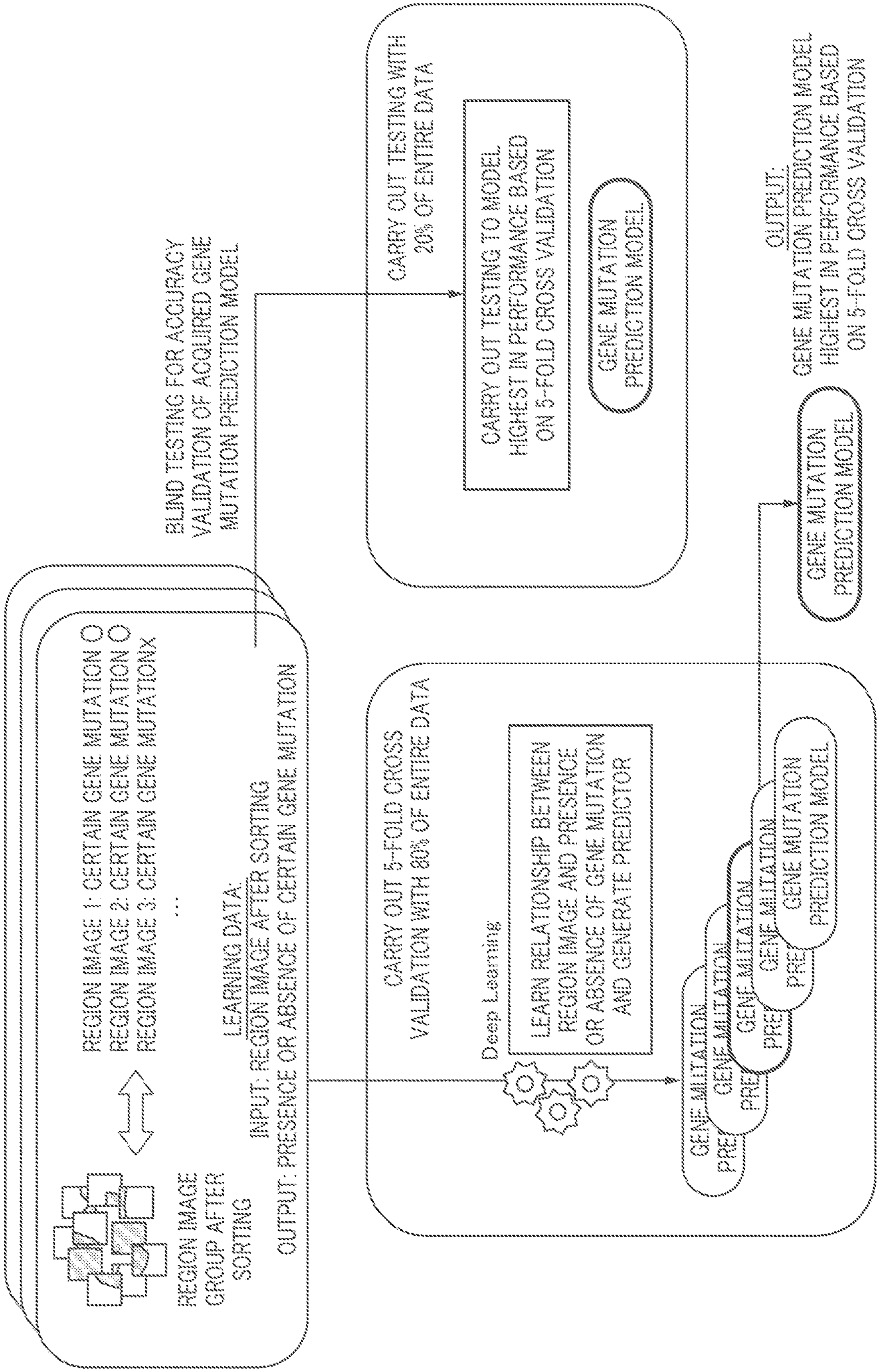
FIG. 7 is a schematic diagram for describing learning and testing at the time of construction of a gene mutation prediction model for a certain gene mutation.

Next, learning and testing at the time of construction of a gene mutation prediction model for a certain gene mutation in step S6 of FIG. 3 will be described with FIG. 7. FIG. 7 is a schematic diagram for describing learning and testing at the time of construction of a gene mutation prediction model for a certain gene mutation. As illustrated in FIG. 7, learning data includes a set of a sorted region image and the presence or absence of a certain gene mutation. Machine learning is carried out with the sorted region image given to the input of a machine learning model and the presence or absence of the certain gene mutation given to the output of the machine learning model. Thus, learning of the relationship between the region image and the presence or absence of the certain gene mutation causes generation of a gene mutation prediction model for predicting the certain gene mutation.

As an example, at the time of learning, 5-fold cross validation is carried out with 80% of the entire learning data. That is, learning is carried out with 64% of the entire learning data and validation is carried out with 16% of the entire learning data. Specifically, validation is carried out as follows. First, 80% of the entire learning data is divided into five. Here, for easy understanding, subsets of data resulting from the division into five are defined as s1, s2, s3, s4, and s5.

For example, after 80% of the learning data is divided into five, first, with the subsets s1, s2, s3, and s4 as training subsets, model learning starts. Subsequently, with s5 as a validation subset, model validation is carried out. The evaluation indicator acquired at the time (e.g., accuracy or F1 score) is defined as el.

Next, learning is carried out with s2, s3, s4, and s5 and evaluation is carried out with s1. Similarly, learning and evaluation are repeated with replacement of the subsets. Learning and evaluation are repeated to all the combinations, so that five evaluation indicators are acquired. Then, the model highest in performance based on the five evaluation indicators is determined as a gene mutation prediction model.

For accuracy validation of the acquired gene mutation prediction model, with 20% of the entire learning data, blind testing is carried out to the model highest in performance based on the 5-fold cross validation. Thus, the performance of the determined gene mutation prediction model is validated, and the gene mutation prediction model is adopted if its performance fulfills the criterion.

A method of setting the "combination of the presence or absence of the histopathological features at the time of sorting" at the time of sorting an region image in a step of predicting an unknown gene mutation of a colorectal cancer patient will be described with FIGS. 8 to 17.

Figure 8:
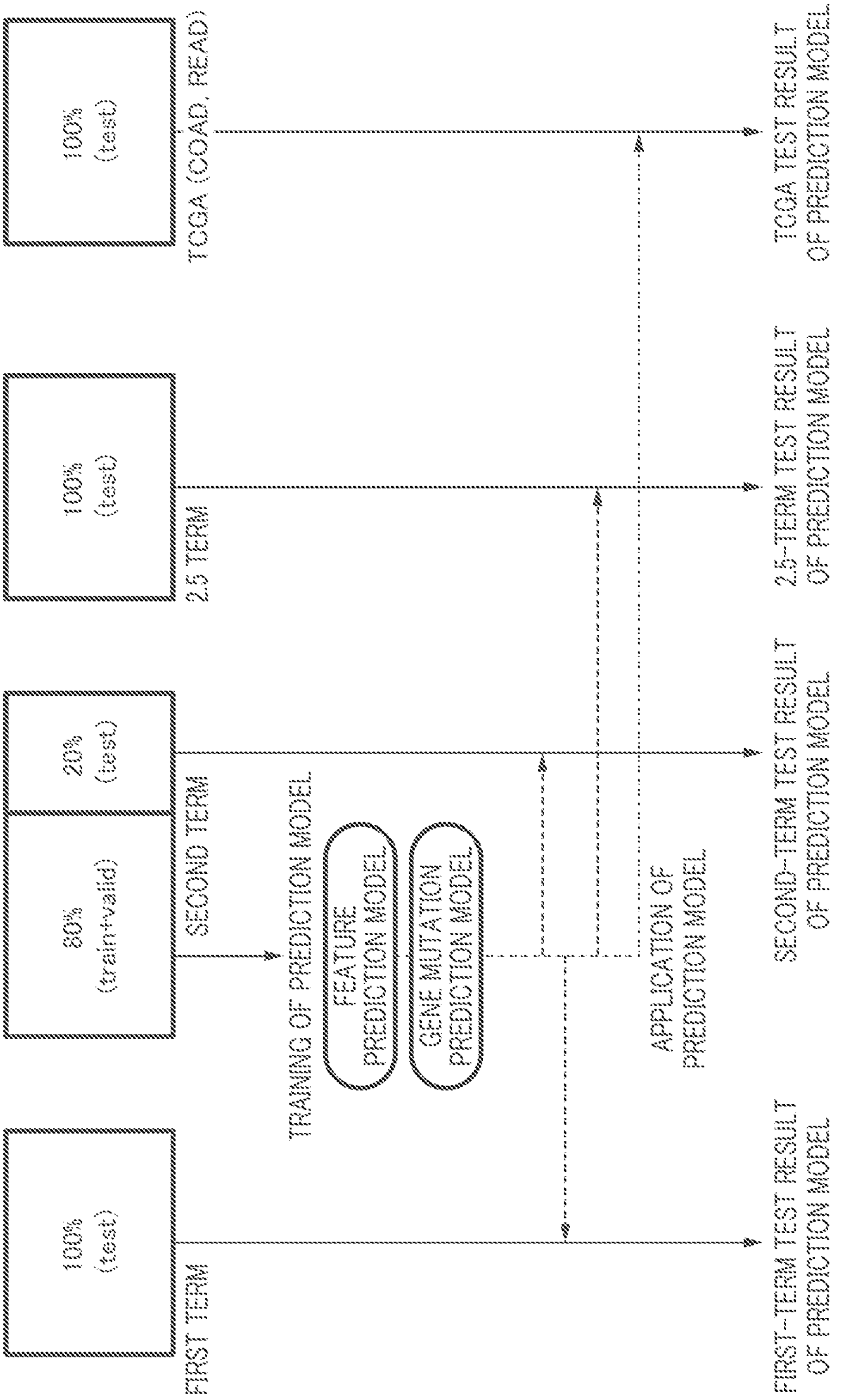
FIG. 8 illustrates an exemplary embodiment of testing of a gene mutation prediction model for colorectal cancer.

FIG. 8 illustrates an exemplary embodiment of testing of a gene mutation prediction model for colorectal cancer. Based on such testing as illustrated in FIG. 8, the "combination of the presence or absence of the histopathological features at the time of sorting" is acquired. Specifically, with 80% of the data in the second term, a feature prediction model and a gene mutation prediction model are trained. The trained feature prediction model and the trained gene mutation prediction model are applied to the data in the first term, the data in the 2.5 term, and the data in TCGA. Here, the data in TCGA is limited to colon adenocarcinoma (COAD) and rectum adenocarcinoma (READ) in colorectal cancer.

<Combination of Features Enabling Prediction of Gene Mutation (or Gene Abnormality)>

As an exemplary embodiment, per type of gene mutation (or gene abnormality) as a target, from all experimental data, a combination of a first feature (primary lesion site) and a second feature (histopathological feature) that fulfills all the following conditions (1) to (3) is sorted.

(1) In a second-term test set, the region under the curve (AUC) indicates 0.8 or more with either a case import technique 1 or a case import technique 2 (namely, a high-accuracy prediction can be made with a cohort used in learning). Here, the AUC corresponds to the region (integral) under the ROC curve with false positive rate as a first axis and true positive rate as a second axis. The region can take on a value in the range of 0 to 1.

(2) In any test set different from the second-term test set, the AUC indicates 0.8 or more with either the case import technique 1 or the case import technique 2 (namely, a high-accuracy prediction can be made with any cohort not used in learning).

(3) The required number of tiles is smallest in combinations identical in image type and feature.

Here, the case import technique 1 and the case import technique 2 are as follows.

(1) Case Import Method 1

The method includes predicting the presence of gene mutation in case 1 in a case where the mean value of the respective prediction values of a gene mutation model to the region images included in an region image group after sorting (e.g., an region image group in FIG. 19) is not less than a threshold th and predicting, otherwise, the absence of gene mutation.

(2) Case Import Method 2

The method includes predicting the presence of gene mutation in the target patient in a case where the ratio of the number of tiles corresponding to region images, each having a prediction value not less than a first threshold th1 based on a gene mutation model, included in an region image group after sorting (e.g., the region image group in FIG. 19) to the total number of region images in the region image group after sorting (e.g., the region image group in FIG. 19) is not less than a second threshold th2 and predicting, otherwise, the absence of gene mutation.

FIG. 9 illustrates, in a case where the target gene mutation is BRAF+, a set of the sorted primary lesion site and the combination of the presence or absence of the histopathological features at the time of sorting. Here, BRAF+ means all BRAF mutations including BRAF V600E.

FIG. 10 illustrates, in a case where the target gene mutation is BRAF V600E+, a set of the sorted primary lesion site and the combination of the presence or absence of the histopathological features at the time of sorting. FIG. 11 illustrates, in a case where the target gene mutation is ERBB2+, a set of the sorted primary lesion site and the combination of the presence or absence of the histopathological features at the time of sorting. FIG. 12 illustrates, in a case where the target gene mutation is TP53+, a set of the sorted primary lesion site and the combination of the presence or absence of the histopathological features at the time of sorting. FIG. 13 illustrates, in a case where the state of gene abnormality is MSI, a set of the sorted primary lesion site and the combination of the presence or absence of the histopathological features at the time of sorting. Here, microsatellite instability (MSI) indicates no gene but a state of gene abnormality. FIG. 14 illustrates, in a case where the target gene mutation is RAS+, a set of the sorted primary lesion site and the combination of the presence or absence of the histopathological features at the time of sorting. FIG. 15 follows FIG. 14. Here, RAS+ means KRAS+ or NRAS+.

Referring to FIGS. 9 to 15, illustrated are the primary lesion site, the combination of the presence or absence of the histopathological features at the time of sorting, the AUC of the case import technique 1 and the AUC of the case import technique 2 with second-term test data, the AUC of the case import technique 1 and the AUC of the case import technique 2 with first-term data, the AUC of the case import technique 1 and the AUC of the case import technique 2 with 2.5-term data, and the AUC of the case import technique 1 and the AUC of the case import technique 2 with TCGA data. Referring to FIGS. 10, 13, 14, 15 and FIGS. 16 and 17 to be described below, the "small solid nest and typical cells" in the column of the "combination of the presence or absence of the histopathological features at the time of sorting" means a small solid nest of typical cells (namely, typical cells form a small solid nest). Similarly, referring to FIGS. 10, 14, 15, and FIGS. 16 and 17 to be described below, the "large solid nest and typical cells" in the column of the "combination of the presence or absence of the histopathological features at the time of sorting" means a large solid nest of typical cells (namely, typical cells form a large solid nest).

Referring to FIGS. 9 to 17, the "oo structure (or cell) and mucus ΔΔ" means the oo structure (or cell) with mucus ΔΔ. Specifically, referring to FIGS. 9, 10, 13, 14, 15, 16, and 17, the "cribriform structure and no mucus present" means the "cribriform structure with no mucus present". Similarly, referring to FIGS. 9, 10, 13, 14, 15, 16, and 17, the "cribriform structure and mucus present" means the "cribriform structure with mucus present". Similarly, referring to FIGS. 10, 14, 15, 16, and 17, the "non-serrated and papillary structure and no mucus present" means the "non-serrated and papillary structure with no mucus present". Similarly, referring to FIGS. 11, 15, 16, and 17, the "trabecular structure and mucus present" means the "trabecular structure with mucus present". Similarly, referring to FIGS. 11, 15, 16, and 17, the "trabecular structure and mucus leakage" means the "trabecular structure with mucus leakage". Similarly, referring to FIGS. 12 and 16, the "signet ring cell and mucus leakage" means the "signet ring cell with mucus leakage". Referring to FIGS. 12, 13, and 16, the "trabecular structure and no mucus present" means the "trabecular structure with no mucus present". Similarly, FIGS. 13, 14, 15, 16, and 17, the "cribriform structure and mucus leakage" means the "cribriform structure with mucus leakage". Similarly, FIGS. 14 and 17, the "signet ring cell and mucus leakage" means the "signet ring cell with mucus leakage". Similarly, FIGS. 14 and 17, the "tubular structure and no mucus present" means the "tubular structure with no mucus present". Similarly, FIGS. 14, 15, and 17, the "non-serrated and papillary structure and mucus present" means the "non-serrated and papillary structure with mucus present". Similarly, FIGS. 15 and 17, the "tubular structure and mucus present" means the "tubular structure with mucus present". Similarly, FIGS. 15 and 17, the "tubular structure and mucus leakage" means the "tubular structure with mucus leakage".

FIG. 16 illustrates exemplary tables stored in the storage 23. FIG. 17 follows FIG. 16. In a BRAF table T1 in FIG. 16, in a case where the target gene mutation is BRAF+, records of a set of the sorted primary lesion site and the combination of the presence or absence of the histopathological features at the time of sorting are accumulated. In a BRAF V600E table T2 in FIG. 16, in a case where the target gene mutation is BRAF V600E, records of a set of the sorted primary lesion site and the combination of the presence or absence of the histopathological features at the time of sorting are accumulated.

In an ERBB2 table T3 in FIG. 16, in a case where the target gene mutation is ERBB2, records of a set of the sorted primary lesion site and the combination of the presence or absence of the histopathological features at the time of sorting are accumulated. In a TP53 table T4 in FIG. 16, in a case where the target gene mutation is TP53, records of a set of the sorted primary lesion site and the combination of the presence or absence of the histopathological features at the time of sorting are accumulated. In an MSI table T5 in FIG. 16, in a case where the state of gene abnormality is MSI, records of a set of the sorted primary lesion site and the combination of the presence or absence of the histopathological features at the time of sorting are accumulated.

In an RAS table T6 in FIG. 17, in a case where the target gene mutation is RAS, records of a set of the sorted primary lesion site and the combination of the presence or absence of the histopathological features at the time of sorting are accumulated.

Figure 18:
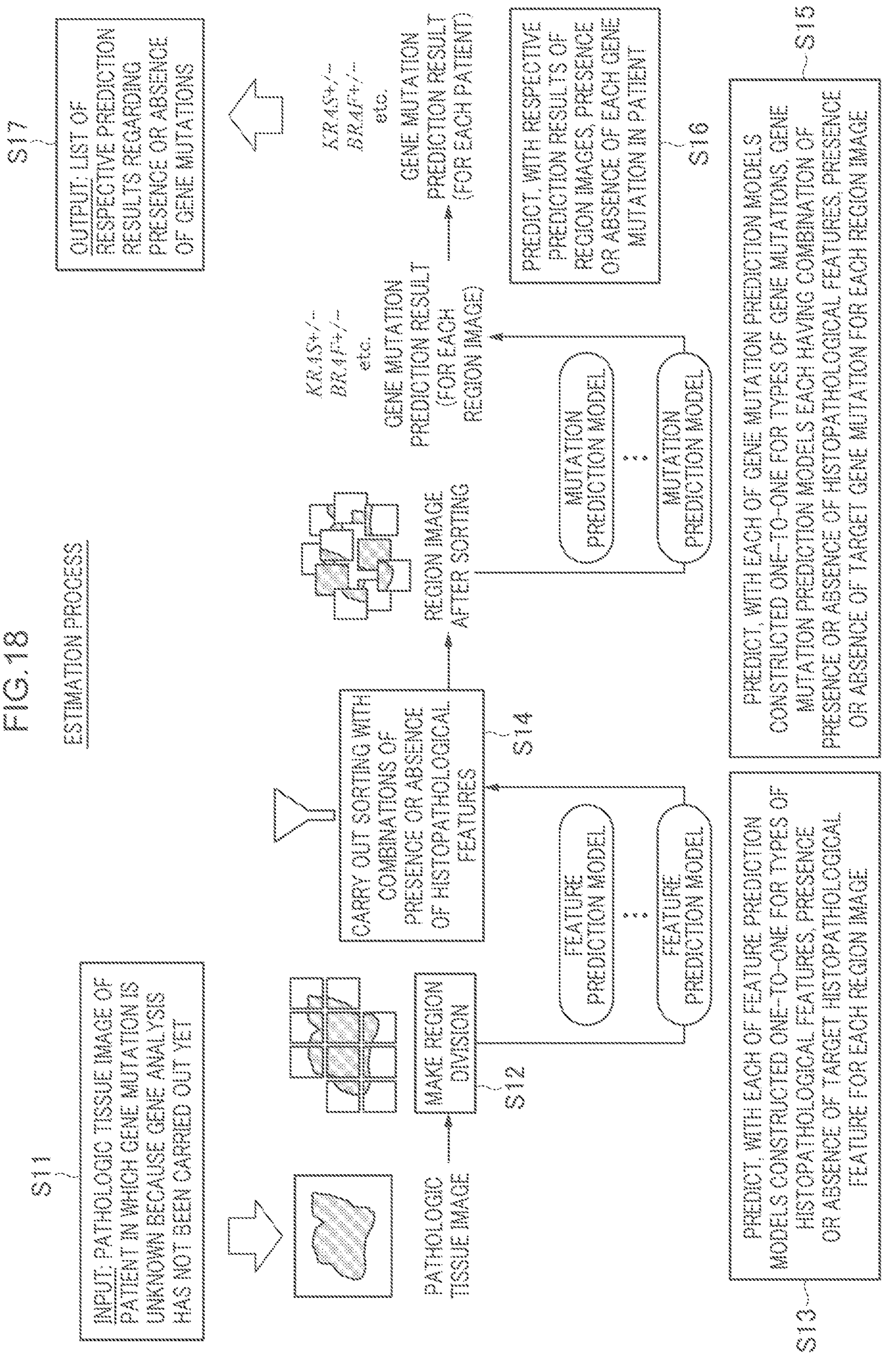
FIG. 18 is a schematic diagram of an estimation process for the presence or absence of each gene mutation.

Next, an estimation process for the presence or absence of each gene mutation will be described with FIG. 18. FIG. 18 is a schematic diagram of an estimation process for the presence or absence of each gene mutation.

(Step S11) First, the acquisition unit 251 acquires a pathologic tissue image of a patient in which gene mutation is unknown because gene analysis has not been carried out yet.

(Step S12) Next, the division unit 252 divides the pathologic tissue image of the patient into a plurality of region images.

(Step S13) Next, with each of feature prediction models constructed one-to-one for types of histopathological features, the feature prediction unit 253 predicts the presence or absence of the target histopathological feature for each region image. More particularly, for example, the feature prediction unit 253 inputs each region image to each of a plurality of feature prediction models constructed one-to-one for types of histopathological features and acquires prediction information on the presence or absence of the histopathological feature.

(Step S14) Next, with the acquired combinations of the presence or absence of the histopathological features, the feature prediction unit 253 sorts the plurality of region images. More particularly, for example, the feature prediction unit 253 extracts, from the plurality of region images, an region image of which the acquired combination of the presence or absence of the histopathological features matches a particular combination of the presence or absence of the histopathological features set for each gene abnormality.

Here, for example, a particular combination of the presence or absence of the histopathological features set to BRAF gene abnormality is one in the "combination of the presence or absence of the histopathological features at the time of sorting" in the BRAF table T1 of FIG. 16. Similarly, for example, a particular combination of the presence or absence of the histopathological features set to BRAF V600E gene abnormality is one in the "combination of the presence or absence of the histopathological features at the time of sorting" in the BRAF V600E table T2 of FIG. 16. Similarly, for example, a particular combination of the presence or absence of the histopathological features set to ERBB2 gene abnormality is one in the "combination of the presence or absence of the histopathological features at the time of sorting" in the ERBB2 table T3 of FIG. 16. Similarly, for example, a particular combination of the presence or absence of the histopathological features set to TP53 gene abnormality is one in the "combination of the presence or absence of the histopathological features at the time of sorting" in the TP53 table T4 of FIG. 16. Similarly, for example, a particular combination of the presence or absence of the histopathological features set to MSI gene abnormality is one in the "combination of the presence or absence of the histopathological features at the time of sorting" in the MSI table T5 of FIG. 16. Similarly, for example, a particular combination of the presence or absence of the histopathological features set to RAS gene abnormality is one in the "combination of the presence or absence of the histopathological features at the time of sorting" in the RAS table T6 of FIG. 16.

(Step S15) Next, with each of gene mutation prediction models constructed one-to-one for types of gene mutations, the gene mutation prediction models each having a combination of the presence or absence of the histopathological features, the gene mutation prediction unit 255 predicts the presence or absence of the target gene mutation for each region image. More particularly, for example, the gene mutation prediction unit 255 inputs each region image selected by sorting to each of gene mutation prediction models constructed one-to-one for types of gene mutations, the gene mutation prediction models each having a combination of the presence or absence of the histopathological features, and acquires prediction information on the presence or absence of the gene mutation.

(Step S16) Next, with respective prediction results of the region images, the prediction result output unit 256 predicts the presence or absence of each gene mutation in the patient.

(Step S17) Next, for example, the prediction result output unit 256 outputs a list of respective prediction results regarding the presence or absence of the gene mutations. Note that a prediction result of the presence or absence of gene mutation does not necessarily correspond to all prediction results of the presence or absence of the gene mutations and thus may be a prediction result of the presence or absence of at least one gene mutation. As above, with acquired prediction information on the presence or absence of gene mutation for each region image, the prediction result output unit 256 outputs a prediction result of the presence or absence of at least one gene mutation in the patient.

In the above example, regarding the target gene mutation, region images that match the "combination of the presence or absence of the histopathological features at the time of sorting" are sorted and the sorted region images are each input to the gene mutation prediction model, resulting in acquisition of respective gene mutation prediction results of the region images. Then, the presence or absence of the target gene mutation in the target patient is predicted with the respective prediction results of the region images. However, this is not limiting. Such a series of steps may be carried out per "combination of the presence or absence of the histopathological features at the time of sorting". In this case, collectively, output may be information as to with which set the presence of the target gene mutation has been predicted in the "combination of the presence or absence of the histopathological features at the time of sorting". Furthermore, the above processing may be performed for a plurality of gene mutations and the above output may be made for the plurality of gene mutations.

Note that the acquisition unit 251 may further acquire the primary lesion site of the target disease. In this case, with the acquired primary lesion site of the target disease together with the acquired combination of the presence or absence of the histopathological features, the sorting unit 254 may sort the plurality of region images.

For example, in order to predict the presence or absence of BRAF gene mutation regarding colorectal cancer, with reference to the BRAF table T1 stored in the storage 23 (refer to FIG. 16), the sorting unit 254 may sort, regarding one record, an region image that matches the "primary lesion site" and the "combination of the presence or absence of the histopathological features at the time of sorting". For example, regarding the first record (record on the first line), the sorting unit 254 may sort an region image of which the primary lesion site is the "large intestine left part" and the combination of the presence or absence of the histopathological features at the time of sorting is the "tumor-cell ratio larger than 50%". Thus, sorting of an region image with the primary lesion site of the target disease leads to a rise in the probability that an region image to be input to a gene mutation prediction model can be limited to an region image relating to the target disease, so that an improvement can be made in the accuracy of prediction of the presence or absence of gene mutation.

In this case, for example, regarding the target gene mutation, region images that match a set of the "primary lesion site" and the "combination of the presence or absence of the histopathological features at the time of sorting" are sorted and the sorted region images are each input to the gene mutation prediction model, resulting in acquisition of respective gene mutation prediction results of the region images. Then, the presence or absence of the target gene mutation in the target patient is predicted with the respective prediction results of the region images. Such a series of steps may be carried out per set of the "primary lesion site" and the "combination of the presence or absence of the histopathological features at the time of sorting". In this case, collectively, output may be information as to with which set of the "primary lesion site" and the "combination of the presence or absence of the histopathological features at the time of sorting" the presence of the target gene mutation has been predicted. Furthermore, the above processing may be performed for a plurality of gene mutations and the above output may be made for the plurality of gene mutations.

Figure 19:
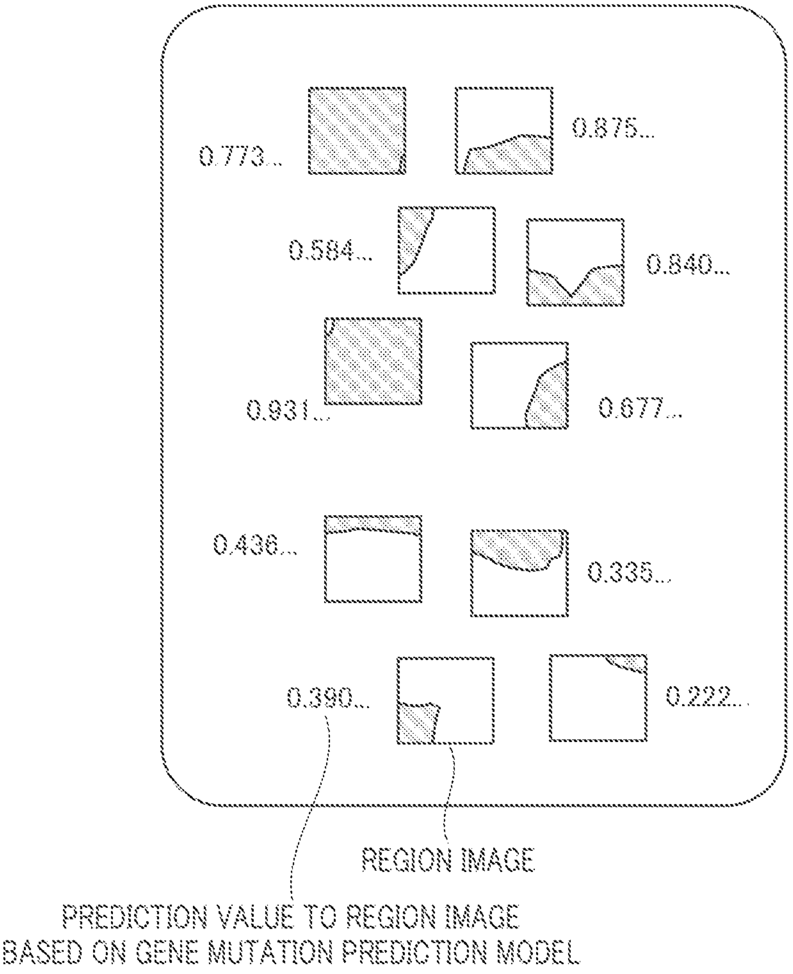
FIG. 19 is a schematic diagram for describing a method for importing from a prediction result to an region image to a prediction result per patient.

Next, a method for importing from a prediction result to an region image to a prediction result per patient will be described with FIG. 19. FIG. 19 is a schematic diagram for describing a method for importing from a prediction result to an region image to a prediction result per patient. FIG. 19 illustrates sets each having an image region after sorting based on the target patient and the prediction value to the region image based on a gene mutation prediction model.

For example, in a case where the number of tiles included in an region image group after sorting (e.g., an region image group in FIG. 19) is K or more, the prediction result output unit 256 predicts the presence or absence of gene mutation at case level with the case import method 1 or the case import method 2. Meanwhile, for example, in a case where the number of tiles is less than K, the prediction result output unit 256 does not carry out prediction of gene mutation at case level (resulting in no gene mutation).

Figure 20:
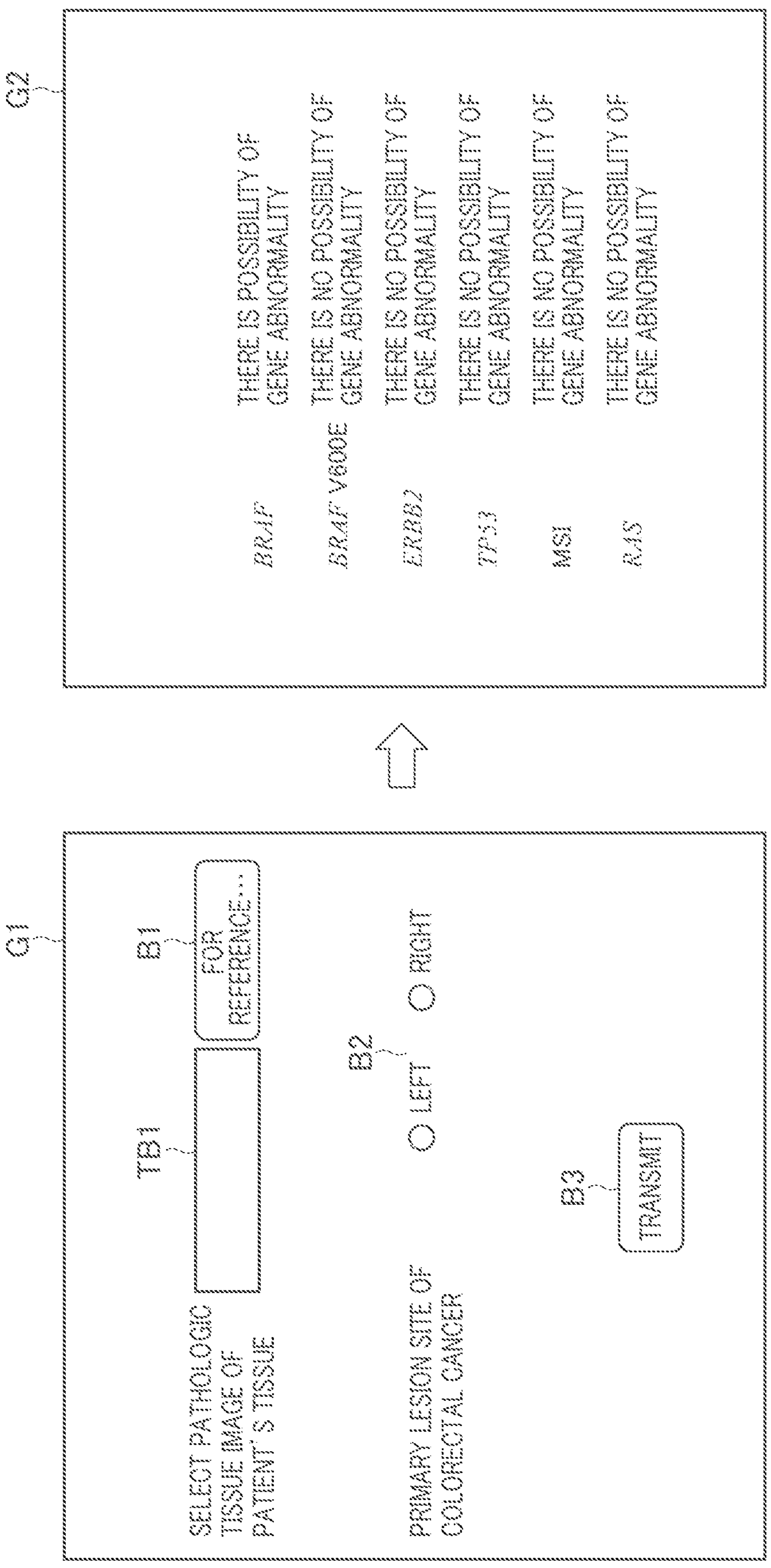
FIG. 20 is a schematic diagram for describing exemplary screen transition on a terminal.

Next, exemplary screen transition on a terminal 1 will be described with FIG. 20. FIG. 20 is a schematic diagram for describing exemplary screen transition on a terminal. As illustrated in FIG. 20, a screen G1 of the terminal 1 is provided with a text box TB1 for input of the path of a pathologic tissue image file for selecting a pathologic tissue image of a patient and a reference button B1 for reference to the pathologic tissue image file. A radio button B2 is provided for selecting a position on a primary lesion site of colorectal cancer. In response to a press on a transmission button B3 with a selected pathologic tissue image of a patient and a selected position on a primary lesion site of colorectal cancer, a transition is made to a screen G2. On the screen G2 after transition, displayed is a list of prediction results of the presence or absence of gene mutations.

Figure 21:
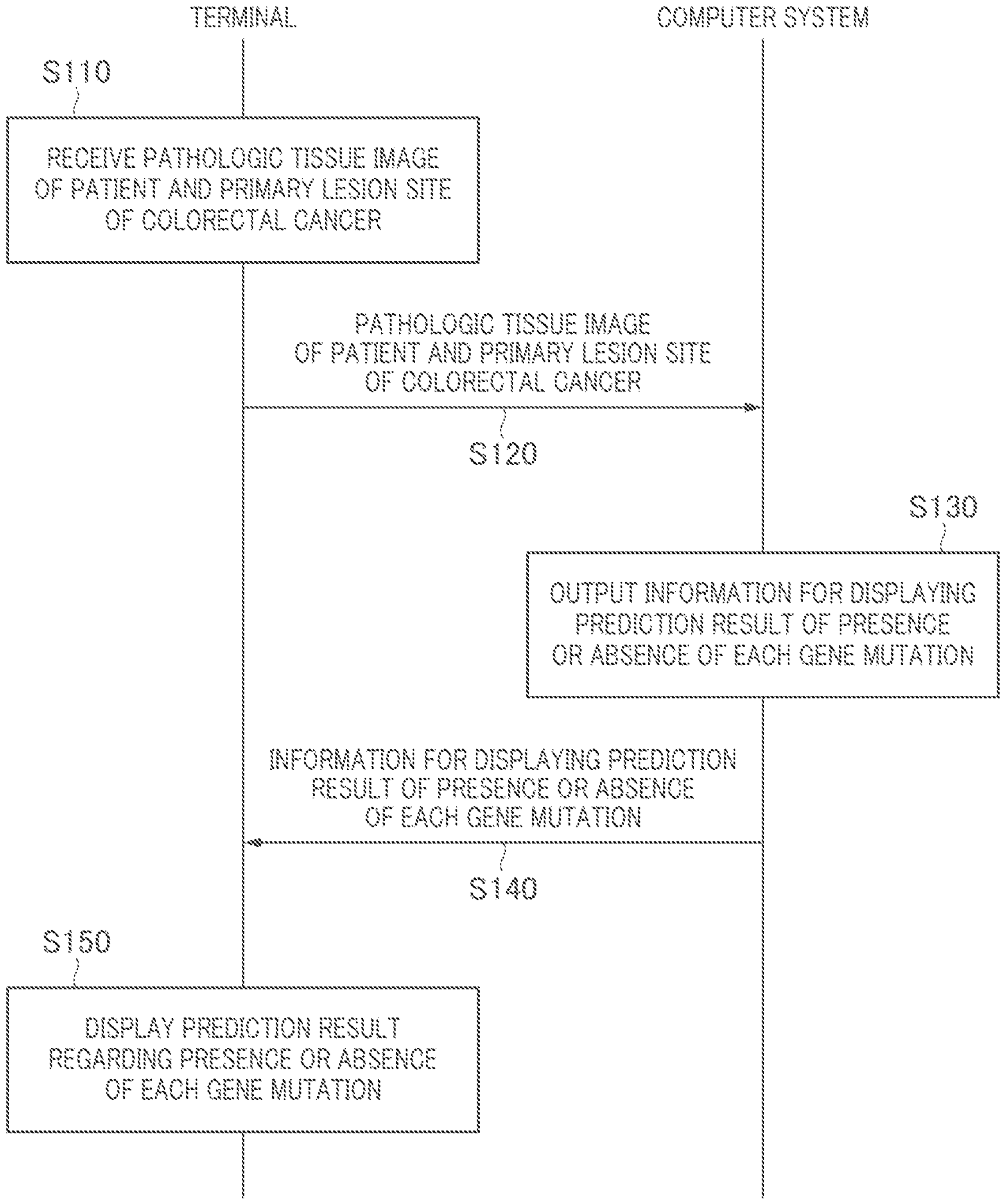
FIG. 21 is a flowchart of an exemplary flow of processing of screen transition in FIG. 20.

Next, a flow of processing of screen transition in FIG. 20 will be described with FIG. 21. FIG. 21 is a flowchart of an exemplary flow of processing of screen transition in FIG. 20.

(Step S110) First, the terminal 1 receives a pathologic tissue image of a patient and a primary lesion site of colorectal cancer.

(Step S120) Next, the terminal 1 transmits, to the computer system 2, the pathologic tissue image of the patient and the primary lesion site of colorectal cancer.

(Step S130) Next, the computer system 2 receives the pathologic tissue image of the patient and the primary lesion site of colorectal cancer, and then outputs information for displaying a prediction result of the presence or absence of each gene mutation, with the pathologic tissue image of the patient and the primary lesion site of colorectal cancer. This processing has been described in detail with FIG. 18, and thus description thereof will be omitted.

(Step S140) Next, the computer system 2 transmits, to the terminal 1, the information for displaying a prediction result of the presence or absence of each gene mutation.

(Step S150) Next, the terminal 1 receives the information for displaying a prediction result of the presence or absence of each gene mutation, and displays a prediction result regarding the presence or absence of each gene mutation, with the information. Then, the processing of the present flowchart terminates.

As above, according to the present embodiment, provided is an information processing system S including: an acquisition unit 251 that acquires a pathologic tissue image of a patient having a target disease; a division unit 252 that divides the pathologic tissue image of the patient into a plurality of region images; a feature prediction unit 253 that inputs each of the plurality of region images to each of a plurality of feature prediction models constructed one-to-one for types of histopathological features, to acquire prediction information on presence or absence of the histopathological features; a sorting unit 254 that sorts a plurality of region images of which respective combinations of presence or absence of the histopathological features based on the acquisition match a previously set combination of presence or absence of the histopathological features at time of sorting; a gene mutation prediction unit 255 that inputs each of the plurality of region images selected by the sorting to each of gene mutation prediction models constructed one-to-one for types of gene mutations, the gene mutation prediction models each having a combination of presence or absence of the histopathological features, to acquire prediction information on presence or absence of the gene mutations; and a prediction result output unit 256 that outputs, with the prediction information on presence or absence of the gene mutations acquired for each region image, a prediction result of presence or absence of at least one gene mutation in the patient.

According to the present embodiment, provided is an information processing system for predicting a gene having mutated in colorectal cancer tissue of a patient having colorectal cancer. The information processing system S includes an acquisition unit 251 that acquires a colorectal-cancer pathologic tissue image of the patient. The information processing system S further includes a division unit 252 that divides the colorectal-cancer pathologic tissue image of the patient into a plurality of region images. The information processing system S further includes a feature prediction unit 253 that inputs each of the plurality of region images to each of a plurality of feature prediction models constructed one-to-one for types of histopathological features, to acquire prediction information on presence or absence of the histopathological features. The information processing system S further includes a sorting unit 254 that sorts a plurality of region images of which respective combinations of presence or absence of the histopathological features based on the acquisition match a combination of presence or absence of the histopathological features at time of sorting previously set to at least one of BRAF, BRAF V600E, ERBB2, RAS, TP53, or MSI. The information processing system S further includes: a gene mutation prediction unit 255 that inputs each of the sorted plurality of region images to each of gene mutation prediction models constructed one-to-one for types of gene mutations, the gene mutation prediction models each having a combination of presence or absence of the histopathological features, to acquire prediction information on presence or absence of the gene mutations; and a prediction result output unit 256 that outputs, with the prediction information on presence or absence of the gene mutations acquired for each region image, a prediction result of presence or absence of at least one gene mutation of BRAF, BRAF V600E, ERBB2, RAS, TP53, or MSI in the patient.

According to the configuration, input of a colorectal-cancer pathologic tissue image of a patient having colorectal cancer enables prompt acquisition of a prediction result of the presence or absence of gene mutation. Thus, with reference to the prediction result, a clinician can prescribe the patient medication corresponding to the prediction result of the presence or absence of gene mutation, so that administration of medication effective against the gene abnormality of the colorectal cancer can be inhibited from being delayed.

According to the present embodiment, provided is an information processing system for estimating presence or absence of BRAF gene mutation in a tumor, the information processing system including: means of dividing a pathologic tissue image of the tumor into one or a plurality of images; means of selecting, from among the divided images, at least one image of an image having a tumor-cell ratio larger than 50%, an image including a papillary structure, an image including a non-serrated and papillary structure, an image including a non-serrated and papillary structure and mucus present, an image including a cribriform structure, an image including a cribriform structure and no mucus present, or an image including a cribriform structure and mucus present; and means of estimating, with the selected at least one image, the presence or absence of the BRAF gene mutation.

According to the configuration, input of a pathologic tissue image enables prompt acquisition of a prediction result of the presence or absence of the BRAF gene mutation. Thus, with reference to the prediction result, a clinician can prescribe the patient medication corresponding to the prediction result of the presence or absence of the BRAF gene mutation, so that administration of medication effective against the BRAF gene abnormality of cancer can be inhibited from being delayed.

According to the present embodiment, provided is an information processing system for estimating presence or absence of BRAF V600E gene mutation in a tumor, the information processing system including: means of dividing a pathologic tissue image of the tumor into one or a plurality of images; means of selecting, from among the divided images, at least one image of an image including a rail pattern, an image including a small solid nest, an image including a small solid nest of typical cells, an image including a large solid nest of typical cells, an image including an elongated elliptic nucleus, an image including mucus present, an image including a non-serrated and papillary structure and no mucus present, an image including a cribriform structure and no mucus present, or an image including a cribriform structure and mucus present; and means of estimating, with the selected at least one image, the presence or absence of the BRAF V600E gene mutation.

According to the configuration, input of a pathologic tissue image enables prompt acquisition of a prediction result of the presence or absence of the BRAF V600E gene mutation. Thus, with reference to the prediction result, a clinician can prescribe the patient medication corresponding to the prediction result of the presence or absence of the BRAF V600E gene mutation, so that administration of medication effective against the BRAF V600E gene abnormality of cancer can be inhibited from being delayed.

According to the present embodiment, provided is an information processing system for estimating presence or absence of ERBB2 gene mutation in a tumor, the information processing system including: means of dividing a pathologic tissue image of the tumor into one or a plurality of images; means of selecting, from among the divided images, at least one image of an image including a trabecular structure and mucus present or an image including a trabecular structure and mucus leakage; and means of estimating, with the selected at least one image as an analysis target, the presence or absence of the ERBB2 gene mutation.

According to the configuration, input of a pathologic tissue image enables prompt acquisition of a prediction result of the presence or absence of the ERBB2 gene mutation. Thus, with reference to the prediction result, a clinician can prescribe the patient medication corresponding to the prediction result of the presence or absence of the ERBB2 gene mutation, so that administration of medication effective against the ERBB2 gene abnormality of cancer can be inhibited from being delayed.

According to the present embodiment, provided is an information processing system for estimating presence or absence of TP53 gene mutation in a tumor, the information processing system including: means of dividing a pathologic tissue image of the tumor into one or a plurality of images; means of selecting, from among the divided images, at least one image of an image including a signet ring cell and mucus leakage, an image including a germ cell, an image including a trabecular structure and no mucus present, or an image including mucus leakage; and means of estimating, with the selected at least one image, the presence or absence of the TP53 gene mutation.

According to the configuration, input of a pathologic tissue image enables prompt acquisition of a prediction result of the presence or absence of the TP53 gene mutation. Thus, with reference to the prediction result, a clinician can prescribe the patient medication corresponding to the prediction result of the presence or absence of the TP53 gene mutation, so that administration of medication effective against the TP53 gene abnormality of cancer can be inhibited from being delayed.

According to the present embodiment, provided is an information processing system for estimating presence or absence of MSI gene abnormality in a tumor, the information processing system including: means of dividing a pathologic tissue image of the tumor into one or a plurality of images; means of selecting, from among the divided images, at least one image of an image including a rail pattern, an image including a trabecular structure and no mucus present, an image having a tumor-cell ratio larger than 50%, an image including a solid nest, an image including a small solid nest of typical cells, an image including an elongated elliptic nucleus, an image including a papillary structure, an image including a germ cell, an image including a non-serrated and papillary structure, an image including a roundish nucleus, an image including a cribriform structure and no mucus present, an image including a cribriform structure and mucus present, or an image including a cribriform structure and mucus leakage; and means of estimating, with the selected at least one image, the presence or absence of the MSI gene abnormality.

According to the configuration, input of a pathologic tissue image enables prompt acquisition of a prediction result of the presence or absence of the MSI gene abnormality. Thus, with reference to the prediction result, a clinician can prescribe the patient medication corresponding to the prediction result of the presence or absence of the MSI gene abnormality, so that administration of medication effective against the MSI gene abnormality of cancer can be inhibited from being delayed.

According to the present embodiment, provided is an information processing system for estimating presence or absence of RAS gene mutation in a tumor, the information processing system including: means of dividing a pathologic tissue image of the tumor into one or a plurality of images; means of selecting, from among the divided images, at least one image of an image including a signet ring cell and mucus leakage, an image including a tubular structure and no mucus present, an image including a trabecular structure and no mucus present, an image including a small solid nest, an image including a large solid nest, an image including a large solid nest of typical cells, an image including a papillary structure, an image including no mucus present, an image including mucus present, an image including a germ cell, an image including a non-serrated and papillary structure, an image including a non-serrated and papillary structure and no mucus present, an image including a non-serrated and papillary structure and mucus present, an image including a cribriform structure, an image including a cribriform structure and no mucus present, an image including a cribriform structure and mucus present, an image including a cribriform structure and mucus leakage, an image including budding present, an image having a tumor-cell ratio larger than 50%, an image including a small solid nest, an image including a small solid nest of typical cells, an image including a large solid nest, an image including an elongated elliptic nucleus, an image including mucus present, an image including mucus leakage, an image including a non-serrated and papillary structure and no mucus present, an image including a cribriform structure, an image including a cribriform structure and no mucus present, an image including a cribriform structure and mucus present, an image including a tubular structure and mucus present, an image including a tubular structure and mucus leakage, an image including a rail pattern, an image including a high-grade cell atypia, an image including a trabecular structure and mucus present, an image including a trabecular structure and mucus leakage, an image including a solid nest, an image including a non-serrated and papillary structure, an image including a non-serrated and papillary structure and mucus present, or an image including a roundish nucleus; and means of estimating, with the selected at least one image, the presence or absence of the RAS gene mutation.

According to the configuration, input of a pathologic tissue image enables prompt acquisition of a prediction result of the presence or absence of the RAS gene mutation. Thus, with reference to the prediction result, a clinician can prescribe the patient medication corresponding to the prediction result of the presence or absence of the RAS gene mutation, so that administration of medication effective against the RAS gene abnormality of cancer can be inhibited from being delayed.

Note that at least part of the computer system 2 in the embodiment described above may be based on hardware or software. In a case where at least part of the computer system 2 is based on software, a program for achieving the function thereof may be stored in a recording medium, such as a flexible disk or a CD-ROM, and a computer may read and execute the program. Such a recording medium is not limited to a detachably attachable recording medium, such as a magnetic disk or an optical disc, and thus may be a fixed recording medium, such as a hard disk drive or a memory.

Such a program for achieving the function of at least part of the computer system 2 may be distributed through a communication channel (including wireless communication), such as the Internet. Furthermore, the program having been encoded, modulated, or compressed may be distributed through a wired channel or a wireless channel, such as the Internet, or the program having been stored in a recording medium may be distributed.

Furthermore, one or a plurality of information apparatuses may cause the computer system 2 to function. In a case where a plurality of information apparatuses is used, a computer provided as one thereof may execute a predetermined program to achieve the function of at least one means of the computer system 2.

All steps in a method according to the present invention may be achieved by automated control with a computer. Each step may be carried out by a computer and proceeding control between steps may be manually carried out. Furthermore, at least part of all steps may be manually carried out.

The present invention is not limited to the above embodiment, and thus embodiments can be made with modifications of the constituent elements without departing from the gist thereof in a practical phase. Various modifications in the present invention can be made with any appropriate combination of a plurality of constituent elements disclosed in the above embodiment. For example, some constituent elements may be removed from all the constituent elements in the embodiment. Furthermore, any appropriate combination of constituent elements may be made between different embodiments.

REFERENCE SIGNS LIST

1 Terminal
2 Computer system
21 Input interface
22 Communication module
23 Storage
24 Memory
25 Processor
250 Output unit
251 Acquisition unit
252 Division unit
253 Feature prediction unit
254 Sorting unit
255 Gene mutation prediction unit
256 Prediction result output unit

The invention claimed is:

1. An information processing system comprising:
an acquisition unit configured to acquire a pathologic tissue image of a patient having a target disease;
a division unit configured to divide the pathologic tissue image of the patient into a plurality of region images;
a feature prediction unit configured to input each of the plurality of region images to each of a plurality of feature prediction models constructed one-to-one for types of histopathological features, to acquire prediction information on presence or absence of the histopathological features;
a selecting unit configured to select a plurality of region images of which respective combinations of presence or absence of the histopathological features based on the acquisition match a previously set combination of presence or absence of the histopathological features at time of selecting;
a gene mutation prediction unit configured to acquire prediction information on presence or absence of the gene mutations by inputting each of the plurality of region images selected by the selecting to each of gene mutation prediction models constructed for a type of gene mutation and for a combination of presence or absence of histopathological features; and
a prediction result output unit configured to output, with the prediction information on presence or absence of the gene mutations acquired for each region image, a prediction result of presence or absence of at least one gene mutation in the patient.

2. The information processing system according to claim 1, wherein
the acquisition unit further acquires a primary lesion site of the target disease, and
the selecting unit selects the plurality of region images, with the acquired primary lesion site of the target disease together with combinations of presence or absence of the histopathological features based on the acquisition.

3. The information processing system according to claim 1, wherein
the plurality of feature prediction models each results from machine learning with learning data including a divided region image of a pathologic tissue image as an input and a histopathological feature given to the divided region image as an output, and
the gene mutation prediction models each result from machine learning with learning data including an region image selected with a combination of presence or absence of the histopathological features as an input and information on presence or absence of a particular gene mutation as an output.

4. An information processing system for predicting a gene having mutated in colorectal cancer tissue of a patient having colorectal cancer, the information processing system comprising:
an acquisition unit configured to acquire a colorectal-cancer pathologic tissue image of the patient;
a division unit configured to divide the colorectal-cancer pathologic tissue image of the patient into a plurality of region images;
a feature prediction unit configured to input each of the plurality of region images to each of a plurality of feature prediction models constructed one-to-one for types of histopathological features, to acquire prediction information on presence or absence of the histopathological features;
a selecting unit configured to select a plurality of region images of which respective combinations of presence or absence of the histopathological features based on the acquisition match a combination of presence or absence of the histopathological features at time of selecting previously set to at least one of BRAF, BRAF V600E, ERBB2, RAS, TP53, or MSI;
a gene mutation prediction unit configured to input each of the selected plurality of region images to each of gene mutation prediction models constructed one-to-one for types of gene mutations, the gene mutation prediction models each having a combination of presence or absence of the histopathological features, to acquire prediction information on presence or absence of the gene mutations; and
a prediction result output unit configured to output, with the prediction information on presence or absence of the gene mutations acquired for each region image, a prediction result of presence or absence of at least one gene mutation of BRAF, BRAF V600E, ERBB2, RAS, TP53, or MSI in the patient.

5. The information processing system according to claim 4, wherein
the acquisition unit further acquires a primary lesion site of the colorectal cancer, and
the selecting unit selects the plurality of region images, with the acquired primary lesion site of the colorectal cancer together with at least one histopathological feature based on the determination.

6. The information processing system according to claim 4, wherein the plurality of feature prediction models each results from machine learning with learning data including a divided region image of a pathologic tissue image as an input and a histopathological feature given to the divided region image as an output, and the gene mutation prediction models each result from machine learning with learning data including an region image selected with a combination of presence or absence of the histopathological features as an input and information on presence or absence of a particular gene mutation as an output.

7. A computer-implemented information processing method comprising:

an acquisition process of acquiring a pathologic tissue image of a patient having a target disease;

a division process of dividing the pathologic tissue image of the patient into a plurality of region images;

a feature prediction process of inputting each of the plurality of region images to each of a plurality of feature prediction models constructed one-to-one for types of histopathological features, to acquire prediction information on presence or absence of the histopathological features;

a selecting process of selecting a plurality of region images of which respective combinations of presence or absence of the histopathological features based on the acquisition match a previously set combination of presence or absence of the histopathological features at time of selecting;

a gene mutation prediction process of acquiring prediction information on presence or absence of the gene mutations by inputting each of the plurality of region images selected by the selecting to each of gene mutation prediction models constructed for a type of gene mutation and for combination of presence or absence of histopathological features; and a prediction result output process of outputting, with the prediction information on presence or absence of the gene mutations acquired for each region image, a prediction result of presence or absence of at least one gene mutation in the patient.

8. A computer-implemented information processing method for predicting a gene having mutated in colorectal cancer tissue of a patient having colorectal cancer, the information processing method comprising:

an acquisition process of acquiring a colorectal-cancer pathologic tissue image of the patient;

a division process of dividing the colorectal-cancer pathologic tissue image of the patient into a plurality of region images;

a feature prediction process of inputting each of the plurality of region images to each of a plurality of feature prediction models constructed one-to-one for types of histopathological features, to acquire prediction information on presence or absence of the histopathological features;

a selecting process of selecting a plurality of region images of which respective combinations of presence or absence of the histopathological features based on the acquisition match a combination of presence or absence of the histopathological features at time of selecting previously set to at least one of BRAF, BRAF V600E, ERBB2, RAS, TP53, or MSI;

a gene mutation prediction process of acquiring prediction information on presence or absence of the gene mutations by inputting each of the selected plurality of region images to each of gene mutation prediction models constructed for a type of gene mutation and for combination of presence or absence of histopathological features; and a prediction result output process of outputting, with the prediction information on presence or absence of the gene mutations acquired for each region image, a prediction result of presence or absence of at least one gene mutation of BRAF, BRAF V600E, ERBB2, RAS, TP53, or MSI in the patient.

9. A non-transitory computer-readable medium storing a program for causing a computer to carry out:

an acquisition process of acquiring a pathologic tissue image of a patient having a target disease;

a division process of dividing the pathologic tissue image of the patient into a plurality of region images;

a feature prediction process of inputting each of the plurality of region images to each of a plurality of feature prediction models constructed one-to-one for types of histopathological features, to acquire prediction information on presence or absence of the histopathological features;

a selecting process of selecting a plurality of region images of which respective combinations of presence or absence of the histopathological features based on the acquisition match a previously set combination of presence or absence of the histopathological features at time of selecting;

a gene mutation prediction process of inputting each of the plurality of region images selected by the selecting to each of gene mutation prediction models constructed one-to-one for types of gene mutations, the gene mutation prediction models each having a combination of presence or absence of the histopathological features, to acquire prediction information on presence or absence of the gene mutations; and a prediction result output process of outputting, with the prediction information on presence or absence of the gene mutations acquired for each region image, a prediction result of presence or absence of at least one gene mutation in the patient.

10. A non-transitory computer-readable medium storing a program for predicting a gene having mutated in colorectal cancer tissue of a patient having colorectal cancer, the program causing a computer to carry out:

an acquisition process of acquiring a colorectal-cancer pathologic tissue image of the patient;

a division process of dividing the colorectal-cancer pathologic tissue image of the patient into a plurality of region images;

a feature prediction process of inputting each of the plurality of region images to each of a plurality of feature prediction models constructed one-to-one for types of histopathological features, to acquire prediction information on presence or absence of the histopathological features;

a selecting process of selecting a plurality of region images of which respective combinations of presence or absence of the histopathological features based on the acquisition match a combination of presence or absence of the histopathological features at time of selecting previously set to at least one of BRAF, BRAF V600E, ERBB2, RAS, TP53, or MSI;

a gene mutation prediction process of inputting each of the selected plurality of region images to each of gene mutation prediction models constructed one-to-one for types of gene mutations, the gene mutation prediction models each having a combination of presence or absence of the histopathological features, to acquire prediction information on presence or absence of the gene mutations; and a prediction result output process of outputting, with the prediction information on presence or absence of the gene mutations acquired for each region image, a prediction result of presence or absence of at least one gene mutation of BRAF, BRAF V600E, ERBB2, RAS, TP53, or MSI in the patient.

11. An information processing system for estimating presence or absence of BRAF gene mutation in a tumor, the information processing system comprising:

means of dividing a pathologic tissue image of the tumor into one or a plurality of images;

means of selecting, from among the divided images, at least one image of an image having a tumor-cell ratio larger than 50%, an image including a papillary structure, an image including a non-serrated and papillary structure, an image including a non-serrated and papillary structure and mucus present, an image including a cribriform structure, an image including a cribriform structure and no mucus present, or an image including a cribriform structure and mucus present; and means of estimating, with the selected at least one image, the presence or absence of the BRAF gene mutation.

12. An information processing system for estimating presence or absence of BRAF V600E gene mutation in a tumor, the information processing system comprising:

means of dividing a pathologic tissue image of the tumor into one or a plurality of images;

means of selecting, from among the divided images, at least one image of an image including a rail pattern, an image including a small solid nest, an image including a small solid nest of typical cells, an image including a large solid nest of typical cells, an image including an elongated elliptic nucleus, an image including mucus present, an image including a non-serrated and papillary structure and no mucus present, an image including a cribriform structure and no mucus present, or an image including a cribriform structure and mucus present; and means of estimating, with the selected at least one image, the presence or absence of the BRAF V600E gene mutation.

13. An information processing system for estimating presence or absence of ERBB2 gene mutation in a tumor, the information processing system comprising:

means of dividing a pathologic tissue image of the tumor into one or a plurality of images;

means of selecting, from among the divided images, at least one image of an image including a trabecular structure and mucus present or an image including a trabecular structure and mucus leakage; and means of estimating, with the selected at least one image as an analysis target, the presence or absence of the ERBB2 gene mutation.

14. An information processing system for estimating presence or absence of TP53 gene mutation in a tumor, the information processing system comprising:

means of dividing a pathologic tissue image of the tumor into one or a plurality of images;

means of selecting, from among the divided images, at least one image of an image including a signet ring cell and mucus leakage, an image including a germ cell, an image including a trabecular structure and no mucus present, or an image including mucus leakage; and means of estimating, with the selected at least one image, the presence or absence of the TP53 gene mutation.

15. An information processing system for estimating presence or absence of MSI gene abnormality in a tumor, the information processing system comprising:

means of dividing a pathologic tissue image of the tumor into one or a plurality of images;

means of selecting, from among the divided images, at least one image of an image including a rail pattern, an image including a trabecular structure and no mucus present, an image having a tumor-cell ratio larger than 50%, an image including a solid nest, an image including a small solid nest of typical cells, an image including an elongated elliptic nucleus, an image including a papillary structure, an image including a germ cell, an image including a non-serrated and papillary structure, an image including a roundish nucleus, an image including a cribriform structure and no mucus present, an image including a cribriform structure and mucus present, or an image including a cribriform structure and mucus leakage; and means of estimating, with the selected at least one image, the presence or absence of the MSI gene abnormality.

16. An information processing system for estimating presence or absence of RAS gene mutation in a tumor, the information processing system comprising:

means of dividing a pathologic tissue image of the tumor into one or a plurality of images;

means of selecting, from among the divided images, at least one image of an image including a signet ring cell and mucus leakage, an image including a tubular structure and no mucus present, an image including a trabecular structure and no mucus present, an image including a small solid nest, an image including a large solid nest, an image including a large solid nest of typical cells, an image including a papillary structure, an image including no mucus present, an image including mucus present, an image including a germ cell, an image including a non-serrated and papillary structure, an image including a non-serrated and papillary structure and no mucus present, an image including a non-serrated and papillary structure and mucus present, an image including a cribriform structure, an image including a cribriform structure and no mucus present, an image including a cribriform structure and mucus present,
an image including a cribriform structure and mucus leakage,
an image including budding present,
an image having a tumor-cell ratio larger than 50%,
an image including a small solid nest,
an image including a small solid nest of typical cells,
an image including a large solid nest,
an image including an elongated elliptic nucleus,
an image including mucus present,
an image including mucus leakage,
an image including a non-serrated and papillary structure and no mucus present,
an image including a cribriform structure,
an image including a cribriform structure and no mucus present,
an image including a cribriform structure and mucus present,
an image including a tubular structure and mucus present,
an image including a tubular structure and mucus leakage,
an image including a rail pattern,
an image including a high-grade cell atypia,
an image including a trabecular structure and mucus present,
an image including a trabecular structure and mucus leakage,
an image including a solid nest,
an image including a non-serrated and papillary structure,
an image including a non-serrated and papillary structure and mucus present, or
an image including a roundish nucleus; and
means of estimating, with the selected at least one image, the presence or absence of the RAS gene mutation.

* * * * *